(12) United States Patent
Morita et al.

(10) Patent No.: US 12,241,106 B2
(45) Date of Patent: Mar. 4, 2025

(54) BIOSURFACTANT-PRODUCING RECOMBINANT MICROORGANISM

(71) Applicants: NATIONAL INSTITUTE OF ADVANCED INDUSTRIAL SCIENCE AND TECHNOLOGY, Tokyo (JP); TOYOBO CO., LTD., Osaka (JP)

(72) Inventors: Tomotake Morita, Tsukuba (JP); Azusa Saika, Tsukuba (JP); Hideaki Koike, Tsukuba (JP); Tokuma Fukuoka, Tsukuba (JP); Dai Kitamoto, Tsukuba (JP); Tomohiro Sugahara, Tsuruga (JP); Shuhei Yamamoto, Osaka (JP); Atsushi Sogabe, Osaka (JP)

(73) Assignees: NATIONAL INSTITUTE OF ADVANCED INDUSTRIAL SCIENCE AND TECHNOLOGY, Tokyo (JP); TOYOBO CO., LTD., Osaka (JP)

( * ) Notice: Subject to any disclaimer, the term of this patent is extended or adjusted under 35 U.S.C. 154(b) by 561 days.

(21) Appl. No.: 17/626,475

(22) PCT Filed: Jul. 8, 2020

(86) PCT No.: PCT/JP2020/026760
§ 371 (c)(1),
(2) Date: Jan. 11, 2022

(87) PCT Pub. No.: WO2021/010264
PCT Pub. Date: Jan. 21, 2021

(65) Prior Publication Data
US 2022/0282296 A1    Sep. 8, 2022

(30) Foreign Application Priority Data

Jul. 18, 2019  (JP) .................................. 2019-133055

(51) Int. Cl.
*C12P 19/44* (2006.01)
*C12N 9/20* (2006.01)
*C12N 15/52* (2006.01)
*C12N 15/81* (2006.01)
*C40B 40/08* (2006.01)

(52) U.S. Cl.
CPC ............... *C12P 19/44* (2013.01); *C12N 9/20* (2013.01); *C12N 15/52* (2013.01); *C12N 15/815* (2013.01); *C12Y 301/01003* (2013.01); *C40B 40/08* (2013.01)

(58) Field of Classification Search
None
See application file for complete search history.

(56) References Cited

FOREIGN PATENT DOCUMENTS

| CN | 103589764 A | 2/2014 |
|---|---|---|
| JP | 2007-185142 A | 7/2007 |
| JP | 2011-182660 A | 9/2011 |
| JP | 2011-182740 A | 9/2011 |
| JP | 2016-191438 A | 11/2016 |
| JP | 2018-052874 A | 4/2018 |
| JP | 2018-113946 A | 7/2018 |
| WO | WO 2000/029604 A1 | 5/2000 |
| WO | WO 2012/146937 A1 | 11/2012 |
| WO | WO 2014/109360 A1 | 7/2014 |
| WO | WO 2017/208791 A1 | 12/2017 |
| WO | WO 2021/039686 A1 | 3/2021 |

OTHER PUBLICATIONS

Chica et al. Curr Opin Biotechnol. Aug. 2005; 16(4):378-84. (Year: 2005).*
Singh et al. Curr Protein Pept Sci. 2017, 18, 1-11 (Year: 2017).*
Saika et al., "Biosynthesis of Mono-Acylated Mannosylerythritol Lipid in an Acyltransferase Gene-Disrupted Mutant of *Pseudozyma tsukubaensis*," *Appl. Microbiol. Biotechnol.*, 102(4): 1759-1767 (2018).
European Patent Office, Extended European Search Report in European Patent Application No. 20856771.9 (Jul. 14, 2023).
Neveu et al., "The *Pseudozyma flocculosa* Actin Promoter Allows the Strong Expression of a Recombinant Protein in the *Pseudozyma* Species," *Appl. Microbiol. Biotechnol.*, 74(6): 1300-1307 (2007).
Japan Patent Office, Office Action in Japanese Patent Application No. 2021-533006 (Mar. 12, 2024).
Fukuoka et al., "Structural characterization and surface-active properties of a new glycolipid biosurfactant, mono-acylated mannosylerythritol lipid, produced from glucose by *Pseudozyma antarctica*," *Appl. Microbiol. Biotechnol.*, 76(4): 801-810 (2007).
Hewald et al., "Identification of a Gene Cluster for Biosynthesis of Mannosylerythritol Lipids in the Basidiomycetous Fungus *Ustilago maydis*," *Appl. Environ. Microbiol.*, 72(8): 5469-5477 (2006).
Kawashima et al., "Extracellular Production of a Mannosylerythritol by a Mutant of *Candida* sp. from n-Alkanes and Triacylglycerols," *J. Ferment. Technol.*, 61(2):143-149 (1983).
Kim et al., "A glycolipid biosurfactant produced from *Candida* sp. SY16," *Abstracts of the Year 1998 Convention of the Society for Fermentation and Bioengineering*, Abstract 934, p. 195 (1998).
Kitamoto et al., "Extracellular Accumulation of Mannosylerythritol Lipids by a Strain of *Candida antarctica*," *Agric. Biol. Chem.*, 54(1): 31-36 (1990).
Kitamoto et al., "Production of Mannosylerythritol Lipids by *Candida antarctica* from Vegetable Oils," *Agric. Biol. Chem.*, 54(1): 37-40 (1990).
Kitamoto et al., "Production of Mannosylerythritol Lipids as Biosurfactants by Resting Cells of *Candida antarctica*," *Biotechnol. Lett.*, 14(4): 305-310 (1992).

(Continued)

*Primary Examiner* — Christian L Fronda
(74) *Attorney, Agent, or Firm* — Leydig, Voit & Mayer, Ltd.

(57) ABSTRACT

Provided is a means for increasing mannosylerythritol lipid (MEL) production efficiency. The present invention is a mannosylerythritol-lipid-producing microorganism transformed with an expression vector having a gene that encodes a lipase under the control of E5Pgap promoter or E5Ptef promoter.

10 Claims, 13 Drawing Sheets

Specification includes a Sequence Listing.

(56) References Cited

OTHER PUBLICATIONS

Morita et al., "Isolation of basidiomycetous yeast *Pseudozyma tsukubaensis* and production of glycolipid biosurfactant, a diastereomer type of mannosylerythritol lipid-B," *Appl. Microbiol. Biotechnol.*, 88(3): 679-688 (2010).

Nakahara et al., "Induction and Characterization of Mutants Assimilability of n-Alkanes in Shake Cultures from a Strain of *Candida* sp.," *J. Ferment. Technol.*, 61(1): 19-23 (1983).

Saika et al., "Enhanced production of a diastereomer type of mannosylerythritol lipid-B by the basidiomycetous yeast *Pseudozyma tsukubaensis* expressing lipase genes from *Pseudozyma antarctica*," *Appl. Microbiol. Biotechnol.*, 101(23-24): 8345-8352 (2017).

Saika et al., "Identification of the gene *PtMAT1* encoding acetyltransferase from the diastereomer type of mannosylerythritol lipid-B producer *Pseudozyma tsukubaensis*," *J. Biosci. Bioeng.*, 126(6): 676-681 (2018).

Saika et al., "Deficiency of biodegradable plastic-degrading enzyme production in a gene-deletion mutant of phyllosphere yeast, *Pseudozyma antarctica* defective in mannoosylerythritol lipid biosynthesis," *AMB Express*, 9(1): 100 (2019).

Japanese Patent Office, International Search Report in International Patent Application No. PCT/JP2020/026760 (Sep. 1, 2020).

U.S. Appl. No. 17/635,911, filed Feb. 16, 2022.

Japanese Patent Office, International Search Report in International Patent Application No. PCT/JP2020/031766 (Oct. 20, 2020).

Avis et al., "Usefulness of Heterologous Promoters in the *Pseudozyma flocculosa* Gene Expression System," *Biosci. Biotechnol. Biochem.*, 72(2): 456-462 (2008).

Faria et al., "Production of Glycolipid Biosurfactants, Mannosylerythritol Lipids, from Pentoses and D-Glucose/D-Xylose Mixtures by *Pseudozyma* Yeast Strains," *Process Biochemistry*, 49(11): 1790-1799 (2014).

Neveu et al., "Cloning of the Glyceraldehyde-3-Phosphate Dehydrogenase Gene from *Pseudozyma flocculosa* and Functionality of its Promoter in two *Pseudozyma* Species," *Antonie van Leeuwenhoek*, 92(2): 245-255 (2007).

European Patent Office, Extended European Search Report in European Patent Application No. 20841145.4 (Jul. 7, 2023).

Huang et al., "Using Non-ionic Surfactant as an Accelerator to Increase Extracellular Lipid Production by Oleaginous Yeast *Cryptococcus curvatus* MUCL 29819," *Bioresour. Technol.*, 274: 272-280 (2019).

Tamano et al., "High-efficiency Extracellular Release of Free Fatty Acids from *Aspergillus oryzae* Using Non-ionic Surfactants," *J. Biotechnol.*, 248: 9-14 (2017).

\* cited by examiner

Fig.2
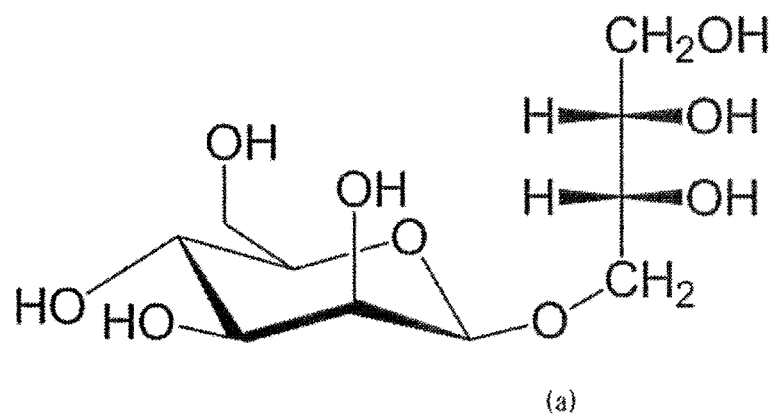
(a)
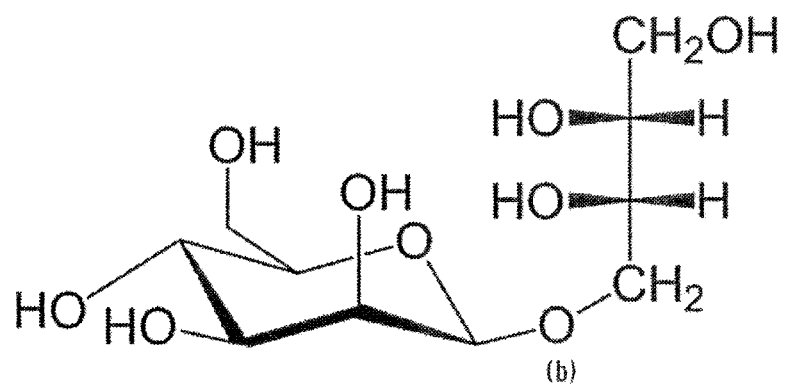
(b)

Fig.6
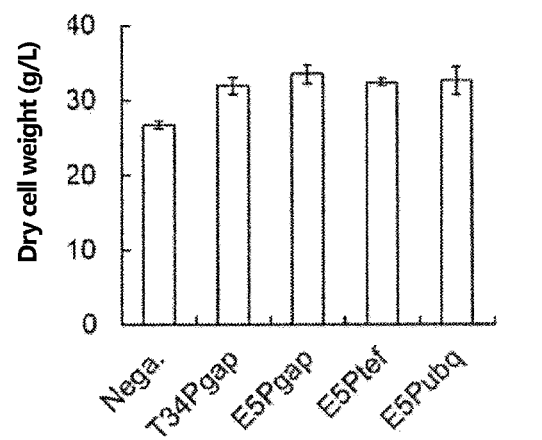
(a)
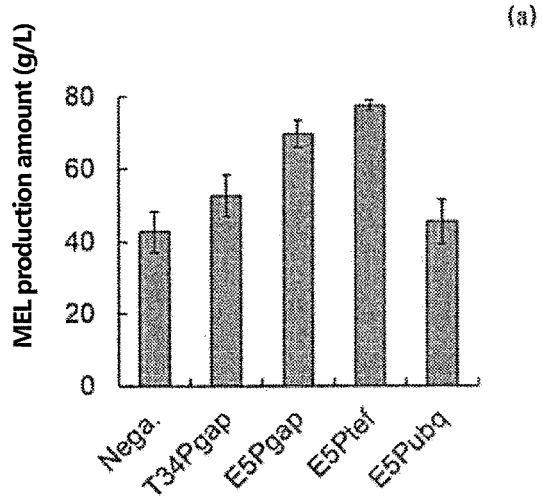
(b)

Fig.8

```
GGAGACATCCGCTCTCTCTTCAGCCTGAGTAAAACCTCTTCCACCGTTTCAACAAGCCGGAGCGCTCCATCGC
TTTCACCCTTCCGCCCATGTGTTGTTCTGTTTGTGTGGAGAAGACGGGCTTGCACAACTGAACACACGCAGAC
CCTTCCGCTTAAGCCTCCTTTCAGCAGCCTCGAGCGTTGACAGCCGGCTAATAGATGCGGAGAAAGAGAAAGC
AAGTGAGCACAGTGACGCCAAGACGCCTGGCGCCTTTGCCGCAAGCAGTGTTCCTTACCATTTGTATTGAGTC
GCATCGCGGACCCTATTCCCTCCGGTATTGCGATACACAGAAAGCAGATCGGCTTTGCTGTGACCGATCTGGT
TCTTCTTTCGGCCGCATTGTGTCTGCGCAATGACTCGATGGAGAGCCGCAGTAAAGCTCAACAAACGTGTGTG
TGTTCTGACTGATTGGTATCAGCGAAAGACCCACCGAAGAATCAGCGCGGAAGATCTCTGAGTGATAAGCTTT
TTTCTTTGCTTGCAGCAGAGAAGAGGGTGCAATTAACACCTGCCAGAAGATGGGCACCTTTTCTATTTCGCGT
CAAATTGAAATGCCCGATTTGGTTGCATGGTCACTTCGAATTGAAACGGTCAACGCTCGGATCAGGGTGTGGA
GTTGAGCTGGATTTCCAGCAGCTTCCTTGCGCGGTGCAGCGCGGTCAGGCCAACTCGATTTTCGGAGTGATTT
TCTGTTCAGATTCAGGAAGAATGGCAGTCAGAGAGAGAAGGAAAGAGGCAGATCGATTGCTCTCTTGCGCCCG
CATCTGCCGCTCACTGTTGCTGCTGCTGCATGTTGATCCCGGAAAGAGTGCGCAGAGCAACTCACTCAGCCAG
CCTTCGTCGGAGAGACTCAAAGGCAAAAGTATAGCAAAAGCACATTCACCATCGTCGCTGTTCTTCCTTCCTC
TCCACCATCGAATCTTTCGTATCCATCCCCTCATCCCAAAAATTATTCACA   (SEQ ID NO: 1)
```

Fig.9

TCGCTCGAAATAACTCAGCACATCGCCCTTGCGCTTTGACCATCCCTGCCCCTCTTGAATTATTACTCAATCC
TCCGATCATAGTCATAGCCCGATGCAGATGCCACGAGACAAGCAGAACTCGACAACATATAGAAAGCCCAGAA
GAAGGACGAGAAGATCTTCCGGCGGGGCGATCAACGGGAGCTTTGCAGACAGCTGGAGCCGAAGAGGAACGTG
CGCGGGAAATGTCTGTCAATACCTTGTCTGACATTGGCAAGGTCTTCTGAGAAGATACACGCACAGTCCACCT
TAGGTCTTCAGAGCGTTCAGAGCGTTCAGAGCGTTCAGACTGTTCAGACAGACAGAGACAGCTCTTCCCGTGG
GAACGTAGCGTTAGAAGGGCGCATTGCAGCAATTGATCTGGTGCTAAAAGTGGCTGTATGCATTTGAATTGGA
GGTGACTTCACTGGCAGTGCAAAGAACATTTCCTGAATACAAGAAAGCTGCAAGGAAGCTTTCTGATGTGAAG
CTCTGTATTGAAAATTGTGATCCCCAATTTCAAATGGCTGTATGCGCTCTTACACACTGTCGGAATGCCTTTT
GATCACAAATTGCAACTCCTGGACGGCGAAGGCGCTCGTTGAAAATTCGGTCTTCTGATTCGAACAAAGCGTT
GTGCTGAGCTGTGGTGGGCTGCCCAGTCTGGTGCAAAGCTCGCTGTGCTTCTTCCAGATTCAATGAGGTCTCG
AGCCTGCCAGTTGGTCCAATCATTGAGGCACACAGGCAGAGGAAGCTGGAAGTTGACCAGCAAGAAAAATTTT
CTTCGCCTGTGAGCGGCGACGAGCAGAGATTTGCCCCCCAAATCTTCGTTTGGCAGGCGTTTGTGCGACGCCC
GCCCGCTCGTCGCAGTGTGCGCGCCCCAGAGCGCCAACAGAATAAAGACCGTCTGATCTCGTCAAAATCTTCC
CTTCTTCCCTCATACATCGTATCATATCATACATCAAAAACATCATCCAAA    (SEQ ID NO: 2)

Fig.10

CAGCCCTTGTTGGAAGATGGGATGGCGATGGAGGATGGGGATGAGTTGCCAGAGGCTGACTTTGCTGCTTCGT
ACAGTCACTTTAGAGATGAGCAGAGGGGTGGAGAGGAGGATGAGGATGCGTTTGATTTGGATCTTAATTGAGA
GCGGACCAGGCTTGAATGTAGGCCGTTGGCGTTGTTGCAGTCGTCAAAGTCAATGAGCGTCCTCAGGTTTAGG
ATCGCGAACGCTACTCTCGCGATGGTTTGGAATGACGGCTCATAGACGTTATCACACATGCTTTACGTTCTCA
CTCCCTCATTGTGTGGAACTTAATAGACATATACCCTTCTGTCGTGCTGTTCGGAGTAAGATAGCGATCTTTG
GCATGCTCATGGTACGGCTTCTGCGAGTCAAAGGGTACACTTCAGTGAAAACGATCGCAATCAATGGGAGTTG
TTAGACCGGGGTCGTCAATCTTTGGGAAAAGTAATTTGAATTATGAGTCAAATTCGTGCGAGACATTGACAGT
GACCGACACGTGACTTTGATTCGAATTTCGCAGTTCTTGAATGCCAAATTTTGGCACTCATTCGGGCAATTGA
CCAGTGTCGTTGCGAAGGTAGGAGAAGACAAGGCAGCAGGGCGAGGAAGAAATTTGACTAACGCCGACAGCTC
AGCCAAGGTCTTCTGAGAGGATAGATGACGGTCGCTTGCCGTTCACTCCTTTCTTCTTCTCCTCACGGTTTCA
AGCAGTAAGTATCTCAACTTTTTGGTCGTGAGCGCACCTCGCTCATCGATCCTCTGATGGCGTCGAACATCAC
AGCATCACAGCATCCAGCATCGATCTGTCAGGACTTGATGATCGATGCTCGTGCTCTGTTGCGCGTTCACTAT
CAGGCCTTTACAGCCTCCGTCTAGATCAGCACATACTGACATTGACGCCATCTCTTCTTGCTCTTTTCAACTC
TCACCATCGCAGAGGACACCACCTATCTGGTTAGCAAAATCGTGACTAAAG (SEQ ID NO: 3)

BIOSURFACTANT-PRODUCING RECOMBINANT MICROORGANISM

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 61,114 bytes ASCII (Text) file named "758774SequenceListing.txt," created Jan. 10, 2022.

TECHNICAL FIELD

A technique for producing a biosurfactant by using a microorganism is disclosed.

BACKGROUND ART

Lipase is an enzyme that breaks down ester bonds of triglycerides, which make up fats and oils such as vegetable oils, into fatty acids and glycerol. Many organisms have lipase. Lipase is used not only in biological reactions, but is also used in many industrial applications.

Biosurfactants are natural surfactants produced by microorganisms. Biosurfactants are highly biodegradable, have a low environmental impact, and possess a variety of beneficial physiological functions. Therefore, their use in the food industry, cosmetics industry, pharmaceutical industry, chemical industry, environmental industry, and like industrial fields is significant in realizing an environmentally harmonious society.

Biosurfactants can be classified into five groups: glycolipid biosurfactants, acyl peptide biosurfactants, phospholipid biosurfactants, fatty acid biosurfactants, and polymeric biosurfactants. Among these, glycolipid surfactants have been the most well studied. Known as glycolipid biosurfactants are mannosylerythritol lipid (hereinafter also referred to as MEL) wherein a fatty acid is ester-linked to mannosylerythritol wherein erythritol is glycosidically linked to mannose (hereinafter also referred to as ME); rhamnolipids, Ustilagic acids, trehalose lipids, sophorose lipid, and the like.

As for MEL, there are many reports on producing MEL from oils and fats, such as vegetable oils. For example, Non-Patent Literature (NPL) 1 and Non-Patent Literature (NPL) 2 report that 35 g/L of MEL (production rate: 0.3 g/L/h, raw material yield: 70 mass %) can be produced from 5 mass % soybean oil in 5 days by using *Candida* sp. strain B-7. Non-Patent Literature (NPL) 3 and Non-Patent Literature (NPL) 4 report that 38 g/L of MEL (production rate: 0.2 g/L/h, raw material yield: 48 mass %) can be produced from 8 mass % soybean oil in 8 days by using *Candida antarctica* strain T-34.

Non-Patent Literature (NPL) 5 reports that 110 g/L (production rate: 0.2 g/L/h, raw material yield: 44 mass %) of MEL can be produced from 25 mass % of peanut oil in 24 days by sequential fed-batch addition three times in total at 6-day intervals using *Candida antarctica* strain T-34. Non-Patent Literature (NPL) 6 reports that using *Candida* sp. strain SY-16, 50 g/L (production rate: 0.25 g/L/h, raw material yield: 50 mass %) of MEL can be produced from 10 mass % of vegetable oil in 200 hours by a fed-batch culture method, and 120 g/L (production rate: 0.6 g/L/h, raw material yield: 50 mass %) of MEL can also be produced from 20 mass % vegetable oil in 200 hours by a flow-through culture method.

MELs have various structures that are different in positions and number of fatty acid residues and acetyl groups that are bound. FIG. 1 shows a structural formula of MEL wherein $R_1$ to $R_5$ each represent a hydrogen atom, an acetyl group, or a $C_{3-18}$ fatty acid residue. The structure in which $R_1$ and $R_2$ are fatty acid residues and $R_3$ and $R_4$ are acetyl groups is defined as MEL-A. The structure in which $R_3$ is a hydrogen atom and $R_4$ is an acetyl group is defined as MEL-B. The structure in which $R_3$ is an acetyl group and $R_4$ is a hydrogen atom is defined as MEL-C. The structure in which $R_3$ and $R_4$ are hydrogen atoms is defined as MEL-D. As shown in FIGS. 2(*a*) and 2(*b*), the structure of the obtained ME is different depending on whether the hydroxymethyl group of erythritol bound to mannose is derived from the carbon at 1-position or the carbon at 4-position. The above *Candida antarctica* strain T-34 produces a compound having, as a sugar backbone, 4-O-β-D-mannopyranosyl-erythritol as shown in FIG. 2(*a*). The obtained 4-O-β-D-mannopyranosyl-erythritol lipid is also referred to as 4-O-β-MEL.

Many kinds of microorganisms produce the above 4-O-β-MEL. In contrast, *Pseudozyma tsukubaensis* produces 1-O-β-D-mannopyranosyl-erythritol Lipid-B (hereinafter also referred to as 1-O-β-MEL-B) having 1-O-β-D-mannopyranosyl-erythritol shown in FIG. 2(*b*) as a sugar backbone by using olive oil as a raw material. 1-O-β-MEL-B is characterized by having enhanced hydrating properties and higher vesicle-forming ability than 4-O-β-MEL-B, and is a promising biomaterial for skin care products etc. *Pseudozyma tsukubaensis* 1E5 has been reported to be capable of producing 70 g/L of 1-O-β-MEL-B (production rate: 0.4 g/L/h, raw material yield: 35 mass %) using 20 mass % of olive oil in 7 days (see Non-Patent Literature (NPL) 7) and is sold as a cosmetic material.

CITATION LIST

Patent Literature

PTL 1: WO2017/208791

Non-Patent Literature

NPL 1: T. Nakahara, H. Kawasaki, T. Sugisawa, Y. Takamori and T. Tabuchi: J. Ferment. Technol., 61, 19 (1983)
NPL 2: H. Kawasaki, T. Nakahara, M. Oogaki and T. Tabuchi: J. Ferment. Technol., 61, 143 (1983)
NPL 3: D. Kitamoto, S. Akiba, C. Hioki and T. Tabuchi: Agric. Biol. Chem., 54, 31 (1990)
NPL 4: D. Kitamoto, K. Haneishi, T. Nakahara and T. Tabuchi: Agric. Biol. Chem., 54, 37 (1990)
NPL 5: D. Kitamoto, K. Fijishiro, H. Yanagishita, T. Nakane and T. Nakahara: Biotechnol. Lett., 14,305 (1992)
NPL 6: Kim, Heidai I, Tohoru Katsuragi, Yoshiki Tani, The Abstracts of the Year 1998 Convention of the Society for Fermentation and Bioengineering, Japan, p. 195
NPL 7: T. Morita, M. Takashima, T. Fukuoka, M. Konishi, T. Imura, D. Kitamoto: Appl. Microbiol. Biotechnol., 88,679 (2010)

SUMMARY OF INVENTION

Technical Problem

In order for MEL to be widely used in the food industry, pharmaceutical industry, chemical industry, etc., increasing MEL production efficiency and reducing its production cost is desirable. As such means for increasing MEL production efficiency, Patent Literature (PTL) 1 discloses transforming a biosurfactant-producing microorganism with a lipase gene. One problem to be solved is to provide further improvement from this measure.

Solution to Problem

To solve this problem, the present inventors conducted extensive research. As a result, the inventors found that the production efficiency of biosurfactants can be dramatically increased by regulating a lipase gene by a specific promoter. As a result of further research and consideration based on this finding, the inventions represented below are provided.

Item 1
A mannosylerythritol-lipid-producing microorganism transformed with an expression vector containing a gene that encodes a lipase under the control of E5Pgap promoter or E5Ptef promoter.

Item 2
The mannosylerythritol-lipid-producing microorganism according to Item 1, wherein the mannosylerythritol-lipid-producing microorganism is a microorganism of the genus *Pseudozyma*.

Item 3
The mannosylerythritol-lipid-producing microorganism according to Item 1 or 2, wherein the gene that encodes a lipase is derived from a microorganism of the genus *Pseudozyma*.

Item 4
The mannosylerythritol-lipid-producing microorganism according to any one of Items 1 to 3, wherein the mannosylerythritol-lipid-producing microorganism is *Pseudozyma tsukubaensis*.

Item 5
An expression vector containing a gene that encodes a lipase under the control of E5Pgap promoter or E5Ptef promoter.

Item 6
The expression vector according to Item 5, wherein the gene that encodes a lipase is derived from a microorganism of the genus *Pseudozyma*.

Item 7
The expression vector according to Item 5 or 6, which is an expression vector for transforming a mannosylerythritol-lipid-producing microorganism.

Item 8
A method for producing the mannosylerythritol-lipid-producing microorganism of Item 1, the method comprising transforming a mannosylerythritol-lipid-producing microorganism with the expression vector of any one of Items 5 to 7.

Item 9
A method for producing a mannosylerythritol lipid using the mannosylerythritol-lipid-producing microorganism of any one of Items 1 to 4.

Item 10
A method for producing a mannosylerythritol lipid, the method comprising culturing the mannosylerythritol-lipid-producing microorganism of any one of Items 1 to 4 in a medium containing a vegetable oil.

Advantageous Effects of Invention

The present invention makes it possible to efficiently produce biosurfactants.

BRIEF DESCRIPTION OF DRAWINGS

FIG. 2 shows the structures of 4-O-β-D-mannopyranosyl-erythritol (a) and 1-O-β-D-mannopyranosyl-erythritol (b).
FIG. 6 shows the amount of bacterial cell growth (a) and MEL production measured by HPLC of the exogenous lipase-transfected strains and the control.
FIG. 8 shows the nucleotide sequence of Pgap derived from *Pseudozyma tsukubaensis*.
FIG. 9 shows the nucleotide sequence of Ptef derived from *Pseudozyma tsukubaensis*.
FIG. 10 shows the nucleotide sequence of Pubq derived from *Pseudozyma tsukubaensis*.

DESCRIPTION OF EMBODIMENTS

Figure 1:
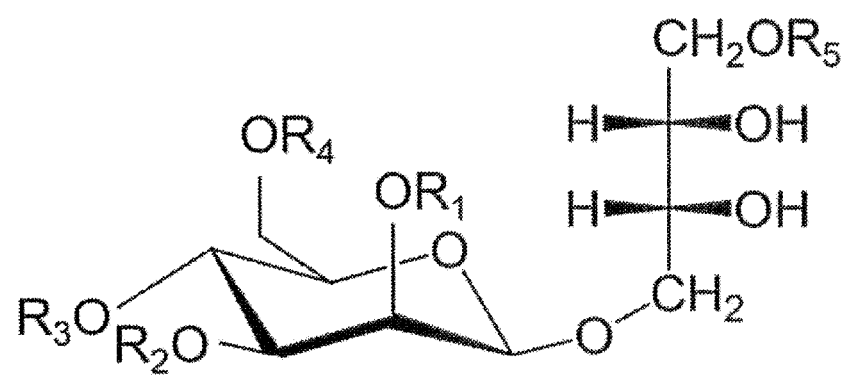
FIG. 1 shows the structure of MEL.

The mannosylerythritol-producing microorganism is preferably transformed with a gene that encodes lipase under the control of a specific promoter. In one embodiment, the specific promoter is a high-expression promoter suitable for the host. In one embodiment, the specific promoter is preferably a promoter derived from a microorganism of the genus *Pseudozyma*, and more preferably a promoter derived from *Pseudozyma tsukubaensis*. In one embodiment, the specific promoter is preferably a promoter of glyceraldehyde triphosphate dehydrogenase gene (Pgap), a promoter of elongation factor EF-1 (Ptef), or a promoter of ubiquitin gene (Pubq) of a microorganism of the genus *Pseudozyma*. In one embodiment, the specific promoter is preferably Pgap or Ptef, and more preferably Ptef. FIG. 8 shows a nucleotide sequence of Pgap derived from *Pseudozyma tsukubaensis* (SEQ ID NO: 1). FIG. 9 shows a nucleotide sequence of Ptef derived from *Pseudozyma tsukubaensis* (SEQ ID NO: 2). FIG. 10 shows a nucleotide sequence of Pubq derived from *Pseudozyma tsukubaensis* (SEQ ID NO: 3). High-expression promoters can be selected by analyzing the expression frequency by RNA sequencing.

In one preferred embodiment, the specific promoter preferably has a nucleotide sequence that is identical to or has 80% or more identity with the nucleotide sequence of any one of SEQ ID NOs: 1 to 3, and more preferably has an identity of 85% or more, 90% or more, 95% or more, 96% or more, 97% or more, 98% or more, or 99% or more. Such promoters can be obtained by any method. For example, such promoters can be produced by using genetic engineering methods and chemical synthesis methods (e.g., liquid-phase methods and solid-phase methods).

In another embodiment, the promoter may comprise a nucleotide sequence represented by one of SEQ ID NOs: 1 to 3 in which one or several nucleotides are substituted, deleted, inserted, added, and/or inverted (hereinafter sometimes collectively referred to as "mutation"), and having promoter activity. The term "several" as used herein means a number corresponding to, for example, less than about 20%, preferably less than about 15%, more preferably less than about 10%, even more preferably less than about 5%, and most preferably less than about 1%, of the total sequence; however, such a number is not limited as long as the promoter activity is maintained. More specifically, for example, the number of nucleotide mutations is 2 to 100, preferably 2 to 80, more preferably 2 to 60, even more preferably 2 to 40, still more preferably 2 to 20, still even more preferably 2 to 15, further still even more preferably 2 to 10, and particularly preferably 2 to 5.

The lipase used for microbial recombination is not limited as long as it is expressed in microorganisms and exhibits lipase activity (i.e., it functions), and can be arbitrarily selected. Thus, the lipase may be derived from any of microorganisms, plants, and animals. In one embodiment, a preferred lipase is derived from a microorganism. In one embodiment, preferred microorganisms from which lipase is derived are the genera *Pseudozyma, Ustilago, Sporisorium, Melanopsichium, Moesziomyces,* and *Kurtzmanomyces*. Preferred examples of microorganisms of the genus *Pseudozyma* are *Pseudozyma antarctica* (*Moesziomyces antarcticus*), *Pseudozyma aphidis* (*Moesziomyces aphidis*), *Pseudozyma hubeiensis,* and *Pseudozyma tsukubaensis*. Preferred examples of microorganisms of the genus *Ustilago* are *Ustilago hordei* and *Ustilago maydis*. Preferred examples of microorganisms of the genus *Sporisorium* are *Sporisorium reilianum* and *Sporisorium scitamineum*. A preferred example of microorganisms of the genus *Melanopsichium* is *Melanopsichium pennsylvanicum*. A preferred example of microorganisms of the genus *Kurtzmanomyces* is *Kurtzmanomyces* sp. I-11.

In one preferred embodiment, the lipase preferably has an amino acid sequence that is identical to or has an identity of 80% or more with the amino acid sequence represented by any one of SEQ ID NOs: 5 to 13. More preferably, the lipase has an identity of 85% or more, 90% or more, 95% or more, 96% or more, 97% or more, 98% or more, or 99% or more. Such a lipase can be obtained by any method, for example, it can be produced by using genetic engineering methods and chemical synthesis methods (e.g., liquid-phase methods and solid-phase methods). The nucleic acid that encodes a lipase can also be obtained by using any method (e.g., genetic engineering methods and chemotropic methods).

SEQ ID NO: 5 is an amino acid sequence of lipase A derived from *P. antarctica* T-34. SEQ ID NO: 6 is an amino acid sequence of a lipase derived from *Pseudozyma aphidis* DSM70725. SEQ ID NO: 7 is an amino acid sequence of a lipase derived from *Pseudozyma hubeiensis* SY62. SEQ ID NO: 8 is an amino acid sequence of a lipase derived from *Ustilago hordei*. SEQ ID NO: 9 is an amino acid sequence of a lipase derived from *Ustilago maydis* 521. SEQ ID NO: 10 is an amino acid sequence of a lipase derived from *Sporisorium reilianum* SRZ2. SEQ ID NO: 11 is an amino acid sequence of a lipase derived from *Sporisorium scitamineum*. SEQ ID NO: 12 is an amino acid sequence of a lipase derived from *Melanopsichium pennsylvanicum* 4. SEQ ID NO: 13 is an amino acid sequence of a lipase derived from *Kurtzmanomyces* sp. I-11. In one embodiment, a preferred lipase is LIP-A derived from *P. antarctica* T-34. *P. antarctica* T-34 is also referred to as "*Moesziomyces antarcticus* T-34." *P. aphidis* is also referred to as "*Moesziomyces aphidis*."

The amino acid sequence identity and nucleotide sequence identity can be calculated by using analysis tools available commercially or through the internet (e.g., software such as FASTA, BLAST, PSI-BLAST, and SSEARCH). For example, the main initial conditions commonly used for BLAST searches are as follows. That is, the amino acid sequence or base sequence identity (%) can be calculated by performing an Advanced BLAST 2.1 search using blastp as a program with the Expect value being set to 10; all Filters being set to OFF; BLOSUM62 being used for Matrix; the Gap existence cost, Per residue gap cost, and Lambda ratio being set to 11, 1, and 0.85 (default values), respectively; and the other various parameters also being set to default values.

In another embodiment, the lipase can be a polypeptide comprising an amino acid sequence represented by one of SEQ ID NOs: 5 to 13 wherein one or several amino acid residues are substituted, deleted, inserted, added, and/or inverted (hereinafter sometimes collectively referred to as "mutation"), and having lipase activity. The "several" as referred to herein is not limited as long as lipase activity is maintained. For example, the "several" means a number corresponding to less than about 20%, preferably less than about 15%, more preferably less than about 10%, even more preferably less than about 5%, and the most preferably less than about 1%, of the total amino acids. More specifically, for example, the number of mutations is 2 to 100, preferably 2 to 80, more preferably 2 to 60, even more preferably 2 to 40, still more preferably 2 to 20, even still more preferably 2 to 15, further still even more preferably 2 to 10, and particularly preferably 2 to 5.

The type of amino acid substitution is not particularly limited; however, it is preferably a conservative amino acid substitution, because it does not give a significant influence on lipase. The "conservative amino acid substitution" refers to a replacement of an amino acid residue with another amino acid residue having a side chain with similar properties. Amino acid residues are classified into various families according to their side chains, such as basic side chains (e.g., lysine, arginine, and histidine), acidic side chains (e.g., aspartic acid and glutamic acid), uncharged polar side chains (e.g., glycine, asparagine, glutamine, serine, threonine, tyrosine, and cysteine), nonpolar side chains (e.g., alanine, valine, leucine, isoleucine, proline, phenylalanine, methionine, and tryptophan), β-branched side chains (e.g., threonine, valine, and isoleucine), and aromatic side chains (e.g., tyrosine, phenylalanine, tryptophan, and histidine). The conservative amino acid substitution is preferably a replacement between amino acid residues of the same family.

One or more mutations can be performed by using known methods, such as a restriction enzyme treatment, a treatment with exonuclease, DNA ligase, or the like, and a site-directed mutagenesis induction method (Molecular Cloning, Third Edition, Chapter 13, Cold Spring Harbor Laboratory Press, New York). Other methods, such as ultraviolet irradiation, may also be used to produce variant lipases. Variant lipases also include naturally occurring variants (e.g., single nucleotide polymorphisms) based on, for example, individual differences in microorganisms carrying lipase, or species or genus differences in microorganisms, etc. In one embodiment, it is preferred that the mutation is present at a site that does not affect the active site or substrate binding site of FGDH.

The nucleotide sequence that encodes the amino acid sequence of SEQ ID NO: 5 is shown in SEQ ID NO: 14. The nucleotide sequence that encodes the amino acid sequence of SEQ ID NO: 6 is shown in SEQ ID NO: 15. The nucleotide sequence that encodes the amino acid sequence of SEQ ID NO: 7 is shown in SEQ ID NO: 16. The nucleotide sequence that encodes the amino acid sequence of SEQ ID NO: 8 is shown in SEQ ID NO: 17. The nucleotide sequence that encodes the amino acid sequence of SEQ ID NO: 9 is shown in SEQ ID NO: 18. The nucleotide sequence that encodes the amino acid sequence of SEQ ID NO: 10 is shown in SEQ ID NO: 19. The nucleotide sequence that encodes the amino acid sequence of SEQ ID NO: 11 is shown in SEQ ID NO: 20. The nucleotide sequence that encodes the amino acid sequence of SEQ ID NO: 12 is shown in SEQ ID NO: 21. The nucleotide sequence that encodes the amino acid sequence of SEQ ID NO: 13 is shown in SEQ ID NO: 22.

The composition of the expression vector is arbitrary as long as the expression vector has a gene that encodes lipase under the control of a specific promoter as described above. For example, the expression vector may have a plurality of genes that encode lipase under the control of a specific promoter. In this case, the plurality of genes that encode lipase may be of the same species or species different from each other. The expression vector may contain a plurality of cassettes comprising genes that encode lipase under the control of a specific promoter. In this case as well, the plurality of genes that encode lipase contained in the expression vector may be of the same species or species different from each other. The specific promoters contained in each cassette may also be of the same species or species different from each other.

The mannosylerythritol-lipid-producing microorganism is preferably transformed with an expression vector having a gene that encodes the lipase under the control of the promoter. The host microorganism to be transformed is not particularly limited as long as it is a microorganism capable of producing a mannosylerythritol lipid (MEL-producing microorganism), and can be arbitrarily selected and used. Examples of the microorganism capable of producing a mannosylerythritol lipid include microorganisms that belong to the genus *Pseudozyma*. In one embodiment, preferred microorganisms capable of producing mannosylerythritol lipids are microorganisms that belong to *Pseudozyma tsukubaensis*, *Pseudozyma antarctica*, *Pseudozyma rugulosa*, *Pseudozyma aphidis*, *Pseudozyma paraantarctica*, and *Pseudozyma hubeiensis*. Preferred examples of MEL-producing strains that belong to the species *Pseudozyma tsukubaensis* include strains NBRC1940, KM-160, 1D9, 1D10, 1D11, 1E5, and JCM16987. The 1-O-β-MEL-B produced by *Pseudozyma tsukubaensis* is more hydratable than 4-O-β-MEL-B and is useful in water-based applications.

The means of transfecting the lipase-encoding nucleic acid into the host cell is arbitrary and is not particularly limited. For example, the nucleic acid can be integrated into a vector suitable as a host, and then the resulting vector is transfected into a host cell by any method. The vector refers to a nucleic acid molecule (carrier) capable of transporting a nucleic acid molecule integrated therein into a cell. The transformation can be a transient or stable transformation. In one embodiment, the transformation is preferably a stable transformation.

The type and structure of the vector are not limited as long as it is capable of replication and expression in the host cell. The type of vector can be selected according to the type of host cell. Specific examples of vectors include plasmid vectors, cosmid vectors, phage vectors, and viral vectors (adenovirus vectors, adeno-associated virus vectors, retrovirus vectors, herpes virus vectors, etc.). In one embodiment, a preferred vector is a plasmid vector.

Examples of plasmid vectors for use when a microorganism of the genus *Pseudozyma* is used as a host include pUXV1 ATCC 77463, pUXV2 ATCC 77464, pUXV5 ATCC 77468, pUXV6 ATCC 77469, pUXV7 ATCC 77470, pUXV8 ATCC 77471, pUXV3 ATCC 77465, pU2X1 ATCC 77466, pU2X2 ATCC 77467, pUXV1-neo, pPAX1-neo, pPAA1-neo, pUC_neo, pUC$_T$_neo, and the like. In one embodiment, preferred vectors are pUXV1-neo, pPAX1-neo, pPAA1-neo, pUC_neo, and pUC$_T$_neo.

The expression vector to be used can be an expression vector containing a selection marker. Insertion of a nucleic acid into the vector, insertion of a selection marker gene, insertion of a promoter, etc. can be performed by using standard recombinant DNA techniques (see, for example, Molecular Cloning, Third Edition, 1.84, Cold Spring Harbor Laboratory Press, New York).

The method for transfecting the vector into a host cell is arbitrary and can be suitably selected according to the host cell, the type of vector, etc. For example, the vector transfection method can be performed by electroporation, calcium phosphate co-precipitation, lipofection, microinjection, the lithium acetate method, and the like. In one embodiment, the method for transfecting the vector into a host cell preferably comprises single-stranding a plasmid vector by restriction enzyme treatment and then transfecting the single-stranded vector into a host cell. This allows for stable transformation by integrating the transfected gene into a genomic gene.

Whether a recombinant microorganism has been obtained by the transfection of nucleic acid can be confirmed by any method. Whether the desired recombinant microorganism has been obtained can be confirmed, for example, by checking the presence or absence of lipase activity imparted by the transfection of an exogenous nucleic acid. The lipase activity can be confirmed by any method.

Since the recombinant microorganism has lipase activity and is capable of producing a mannosylerythritol lipid, the recombinant microorganism can more efficiently produce a mannosylerythritol lipid. The type of mannosylerythritol lipids produced by the recombinant microorganism is not limited and can be selected according to the purpose. In one embodiment, preferred MELs are 1-O-β-MEL-B and 4-O-β-MEL-B, and more preferably 1-O-β-MEL-B. The 4-O-β-MEL-B is also any of MEL-A, MEL-B, MEL-C, and MEL-D.

The production of MEL using a recombinant microorganism can be carried out by any method. For example, MEL can be produced by culturing a recombinant microorganism in a medium suitable for the production of MEL. In one embodiment, when MEL is produced using a recombinant microorganism, a vegetable oil is preferably added to the culture medium. The type of vegetable oil is not particularly limited and can be suitably selected, for example, according to the type of MEL to be produced. Examples of vegetable oils and fats include soybean oil, olive oil, rapeseed oil, safflower oil, sesame oil, palm oil, sunflower oil, coconut oil, cocoa butter, castor oil, and the like. In one embodiment, a preferred fat or oil is olive oil.

The conditions for culturing the recombinant microorganism are not particularly limited. For example, when the recombinant microorganism belongs to the genus *Pseudozyma*, the microorganism can be cultured for 3 to 7 days at a pH of 5 to 8, preferably pH 6, and at a temperature of 20 to 35° C., and preferably 22 to 28° C. MEL can be recovered from the culture liquid according to usual methods.

EXAMPLES

The present invention is described below in more detail with reference to the Examples. However, the present invention is not limited thereto or thereby.

1. Materials
   Bacterial cells to be used
   *Pseudozyma tsukubaensis* strain 1E5 (Deposit No. JCM16987)
   mRNA
   *Pseudozyma tsukubaensis* strain 1E5
   Genomic DNA
   *Pseudozyma tsukubaensis* strain 1E5
   *Pseudozyma antarctica* strain T-34 (deposit No. KM-34),
   Plasmid
   Expression vector $pUC_{T\_}neo$,
   Media
   YM medium containing glycerol: prepared by dissolving 3 g of a yeast extract, 3 g of a malt extract, 5 g of peptone, 10 g of glucose, and 50 g of glycerol in 1 L of deionized water. MEL production medium: prepared by dissolving 5 g of a yeast extract, 3 g of sodium nitrate, 0.3 g of potassium dihydrogen phosphate, 0.3 g of magnesium sulfate hemihydrate, and 20 g of glycerol in 1L of deionized water.

2. RNA Sequencing Analysis 2-1. Culture of Bacterial Strains

The *Pseudozyma tsukubaensis* strain 1E5 was inoculated into 30 mL of MEL medium containing 4% olive oil, and cultured at 25° C. for 2 days with shaking.

2-2. Extraction of Total RNA

The bacterial cells contained in the cell culture liquid were recovered, frozen with liquid nitrogen, and treated with Isogen (produced by Nippon Gene). The aqueous layer containing total RNA was then collected. The collected aqueous layer was treated with phenol and chloroform to extract the total RNA. The purity and quantity of the obtained total RNA were confirmed by spectrophotometer.

2-3. Purification of mRNA

The extracted total RNA was purified with an Oligotex-dT30<super> mRNA Purification Kit (produced by Takara) to obtain mRNA. The purity and quantity of the obtained mRNA were confirmed by spectrophotometry.

2-4. Preparation of RNA Library

The extracted mRNA was processed by using an NEB Next Ultra RNA Library Prep Kit for Illumina (New England Biolabs) and an NEB Next Multiplex Oligos for Illumina (New England Biolabs) according to the manuals attached to the kits to prepare libraries.

2-5. Sequence Analysis

The prepared libraries were subjected to sequence analysis by using a MiSeq Reagent Kit v2 (produced by Illumina). MiSeq (produced by Illumina) was used as a sequencer.

2-6. Data Analysis

The data obtained from the sequence analysis were mapped with Bowtie2 against the gene sequence encoding a protein of the microorganism. About 15% of the sequence analysis data could be attributed to the protein gene sequences. The results were subjected to text processing using BEDtools, which is a mapping data conversion tool, and the programming language Perl, whereby the number of mappings was counted for each protein gene and used as the original data for the expression level of each gene. Since each protein gene has a different number of bases, the longer the gene, the larger the number of mappings. Therefore, when a comparison is made between genes, the number of mappings does not reflect differences in expression levels. To eliminate this influence, the number of mappings is corrected by gene length and the number of mappings per kbp was computed. From the results of analysis, the gap promoter, tef promoter, and ubq promoter were selected as high-expression promoters.

3. Construction of Lipase Expression Vectors Using High-Expression Promoters 3-1. Extraction of Genomic DNA The cells contained in the cell culture liquid of the above *Pseudozyma tsukubaensis* strain 1E5 and *Pseudozyma antarctica* strain T-34 were collected, frozen with liquid nitrogen, and treated with phenol and chloroform to extract genomic DNA. The purity and quantity of the obtained genomic DNA were confirmed by a spectrophotometer.

3-2. Construction of Expression Vectors

Figure 3:
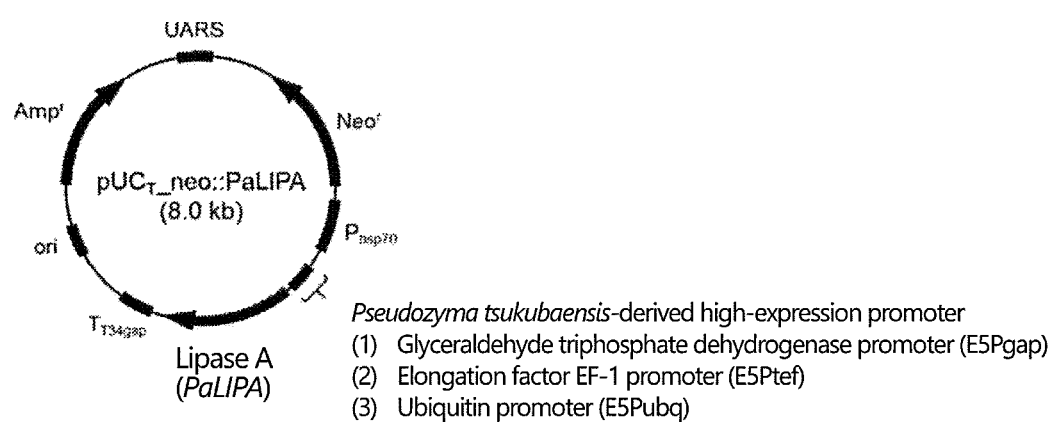
FIG. 3 shows the structure of the expression vector pUC$_{T}$_neo::PaLIPA.

An expression vector that expresses the gene shown in SEQ ID NO: 5 was constructed by the following procedure. SEQ ID NO: 5 is a nucleotide sequence that encodes lipase A of *Pseudozyma antarctica* strain T-34. First, with reference to SEQ ID NO: 5, a forward primer (SEQ ID NO: 23) in which a 15-bp sequence homologous to the vector had been added upstream of the start codon, and a reverse primer (SEQ ID NO: 24) in which a 15-bp sequence homologous to the vector had been added downstream of the stop codon were prepared. Using these primers, gene amplification was performed by using as a template the genomic DNA of *Pseudozyma antarctica* strain T-34 obtained above in 3-1. The amplified gene was ligated to an expression vector $pUC_{T\_}neo$ cleaved at the SmaI site (containing a replication initiation site (UARS) derived from filamentous fungus (*Ustilago maydis*), a G418 resistance gene, and a gap terminator derived from *Pseudozyma antarctica* strain T-34) by using an In-Fusion Cloning Kit (Takara). Subsequently, using the genomic DNA of *Pseudozyma antarctica* strain T-34 or *Pseudozyma tsukubaensis* strain 1E5 as a template, amplification was performed using forward primers (SEQ ID NOs: 25 and 26) in which a SalI site had been added upstream of the sequence of the gap promoter (T34Pgap or E5Pgap; SEQ ID NOs: 4 and 1) and reverse primers (SEQ ID NOs: 27 and 28) in which an XbaI site had been added downstream of the sequence of the gap promoter. Similarly, using the genomic DNA of *Pseudozyma tsukubaensis* strain 1E5 as a template, amplification was performed using forward primers (SEQ ID NOs: 29 and 30) in which a 15-bp sequence homologous to the vector had been added upstream of the sequences of a tef promoter (E5Ptef, SEQ ID NO: 2) and a ubq promoter (E5Pubq, SEQ ID NO: 3), and reverse primers (SEQ ID NOs: 31 and 32) in which a 15-bp sequence homologous to the vector had been added downstream of the sequences of the promoters. Using a Ligation High Ver. 2 (Toyobo, T34Pgap and E5Pgap) or an In-Fusion Cloning Kit (Takara, E5Ptef and E5Pubq), each amplified promoter was ligated to $pUC_{T\_}neo$ into which lipase A cleaved at the SalI site and the XbaI site had been introduced. A gene expression vector $pUC_{T\_}neo::PaLIPA$ that expresses lipase A gene under the control of T34Pgap, E5Pgap, E5Ptef, or E5Pubq promoter was thus constructed. FIG. 3 shows the structure of the expression vector.

```
Fwd:
    (for lipase A amplification, SEQ ID NO: 23)
CTCTAGAGATCCCCATGCGAGTGTCCTTGCGC Rvs:
    (for lipase A amplification, SEQ ID NO: 24)
GTAGGAGCGTACCCCTAAGGCGGTGTGATGGG Fwd:
    (for T-34Pgap amplification, SEQ ID NO: 25)
GTAGTCGACGTCGCCTCGGAAAGATC Fwd:
    (for E5Pgap amplification, SEQ ID NO: 26)
CAGGTCGACATCCGCTCTCTTC Rvs:
    (for T-34Pgap amplification, SEQ ID NO: 27)
CTGTCTAGAGATGATGGATGGGGAGTGTG Rvs
    (for E5Pgap amplification, SEQ ID NO: 28)
TTCCTCTAGATAATTTTTGGGATGAG Fwd:
    (for E5Ptef amplification, SEQ ID NO: 29)
ATGCTCTCAGGTCGACGACGAATAACTCAGCACATCGCCCTTG Fwd:
    (for E5Pubq amplification, SEQ ID NO: 30)
ATGCCTGCAGGTCGACTTGTTGGAAGATGGGATG Rvs:
    (for E5Ptef amplification, SEQ ID NO: 31)
ATGGGATCCTCTAGATGATGTTTTTGATGTATGATG Rvs:
    (for E5Pubq amplification, SEQ ID NO: 32)
ATGGGATCCTCTAGATCACGATTTTGCTAACCAG
```

4. Preparation of Transformants

A gene expression vector pUC$_T$_neo::PaLIPA obtained above in 3-2, which expresses lipase A gene under the control of T34Pgap, E5Pgap, E5Ptef, or E5Pubq promoter, was linearized by restriction enzyme SspI treatment. Using the vector thus obtained, Pseudozyma tsukubaensis strain 1E5 was transformed by electroporation. As a control, the vector pUC$_T$_neo without insert was also linearized by restriction enzyme SspI treatment and then transfected into Pseudozyma tsukubaensis strain 1E5 by electroporation. For the selection of the transformants, G418 was used.

5. Detection of Lipase in Culture Supernatant by SDS-PAGE Method

Each transformant was cultured with shaking in 2 mL of YM medium containing glycerol at 25° C. for 2 days to obtain a pre-culture liquid. Subsequently, 1 mL of the pre-culture liquid was inoculated into 20 mL of MEL medium containing 1% olive oil, and cultured with shaking at 25° C. for 3 days. The resulting cell culture liquid was centrifuged to obtain a culture supernatant. After the culture supernatant was subjected to electrophoresis using Any kD™ Mini-PROTEAN (trademark) TGX™ Precast Protein Gels (Bio-Rad) and Mini-PROTEAN (trademark) Tetra Vertical Electrophoresis Cell (Bio-Rad), the obtained proteins were stained with SimplyBlue™ SafeStain (Invitrogen) to detect lipase (FIG. 4).

Figure 4:
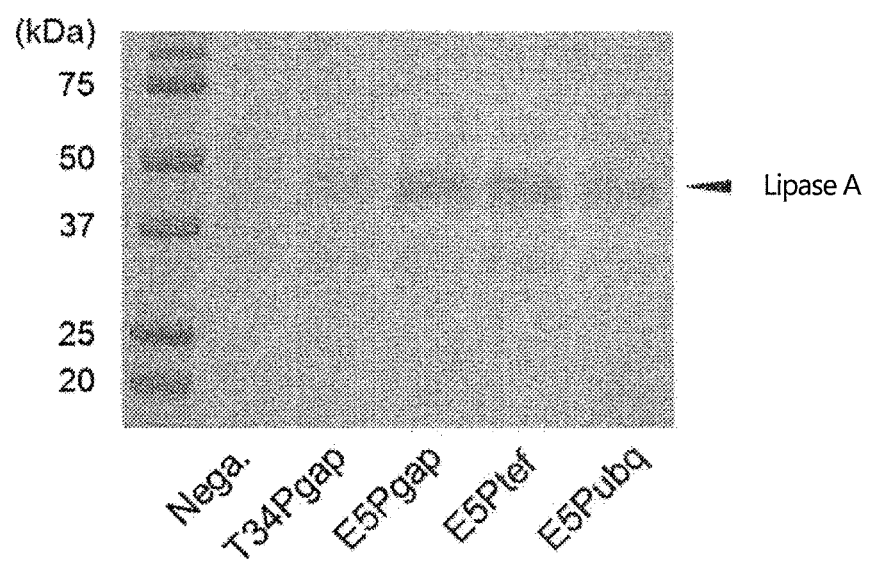
FIG. 4 shows the results of detecting lipase in a culture supernatant by the SDS-PAGE method when exogenous lipase-transfected strains and a control were cultured.

In FIG. 4, Nega. shows a pUC$_T$_neo-transfected strain (control); T34Pgap shows a pUC$_T$_neo::PaLIPA (T34Pgap)-transfected strain; E5Pgap shows a pUC$_T$_neo::PaLIPA (E5Pgap)-transfected strain; E5Ptef shows a pUC$_T$_neo::PaLIPA (E5 Ptef)-transfected strain; and E5Pubq shows a pUC$_T$_neo::PaLIPA (E5Pubq)-transfected strain. As shown in FIG. 4, a more intense band derived from lipase A was detected in the strains transfected with expression vectors using three types of promoters of E5Pgap, E5Ptef, and E5Pubq derived from Pseudozyma tsukubaensis strain 1E5 than the control or the strain transfected with an expression vector using a T34Pgap derived from Pseudozyma antarctica strain T-34. The results thus confirmed that the expression level of lipase in the culture supernatant was improved.

6. Measurement of Enzyme Activity

Each transformant was cultured with shaking in 2 mL of YM medium containing glycerol at 25° C. for 2 days to obtain a pre-culture liquid. Subsequently, 1 mL of the pre-culture liquid was inoculated into 20 mL of MEL medium containing 1% olive oil, and cultured with shaking at 25° C. for 3 days. The obtained cell culture liquid was centrifuged to obtain a culture supernatant. After centrifugation, the cells were collected, dried, and then weighed to evaluate the cell proliferation. No significant difference in the amount of proliferation was observed between the transformants (FIG. 5(a)).

Lipase activity in the culture supernatant of each transformant was measured using a Lipase Activity Assay Kit (Cayman Chemical). The amount of enzyme required to consume 1 nmol of the substrate per minute was defined as 1 Unit (FIG. 5(b)).

Figure 5:
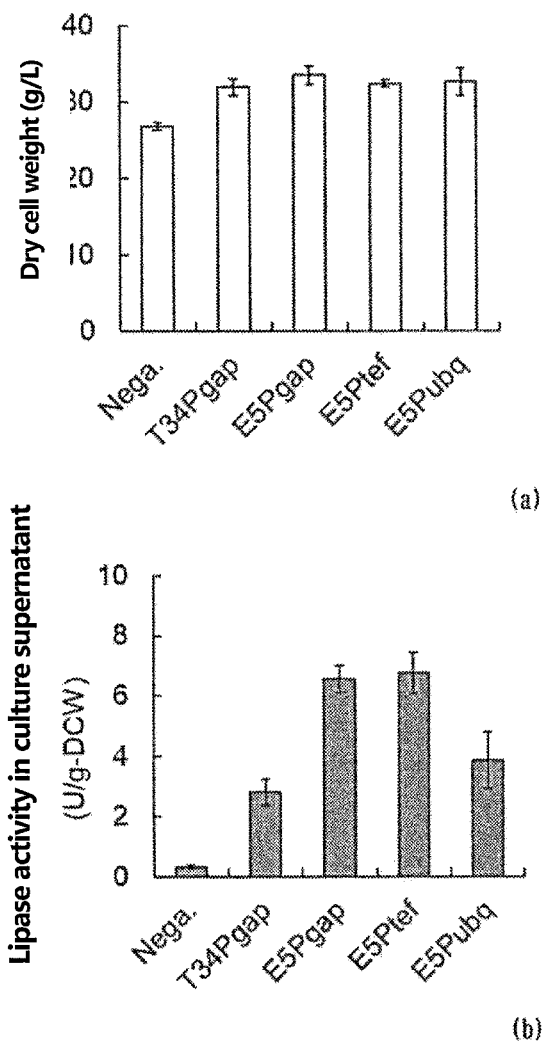
FIG. 5 shows the results of measuring the amount of bacterial cell growth (a) and lipase activity (b) of the exogenous lipase-transfected strains and the control.

As shown in FIG. 5, the strains transfected with expression vectors using E5Pgap, E5Ptef, and E5Pubq promoters, i.e., three types of promoters derived from Pseudozyma tsukubaensis strain 1E5, were confirmed to have significantly higher lipase activity than the control or the strain transfected with an expression vector using T34Pgap derived from Pseudozyma antarctica strain T-34. In particular, the strains transfected with expression vectors using E5Pgap and E5Ptef were confirmed to have lipase activity that was at least twice as high as that of the strain transfected with an expression vector using T34Pgap derived from Pseudozyma antarctica strain T-34.

7. Evaluation of MEL Production Ability of Transformants

Each transformant was cultured with shaking in 2 mL of YM medium containing glycerol at 25° C. for 2 days to obtain a pre-culture liquid. Subsequently, 1 mL of the pre-culture liquid was inoculated into 20 mL of MEL medium containing 6% olive oil and cultured with shaking at 25° C. for 7 days. On the third day and fifth day of the culture, 6% olive oil was added (total amount of oil added: 18%). After the same amount of ethyl acetate was added to the obtained cell culture liquid and stirred well, the ethyl acetate layer was obtained by separation. After addition of methanol to the remaining aqueous layer, the resulting mixture was centrifuged. The precipitated cells were collected and dried, and then weighed. No significant difference in the amount of proliferation was observed between the transformants (FIG. 6(a)). The MEL contained in the ethyl acetate layer was quantified by using high-performance liquid chromatography (HPLC) (FIG. 6(b)).

As shown in FIG. 6, the strains transfected with expression vectors using E5Pgap, E5Ptef, and E5Pubq promoters, i.e., three types of promoters derived from Pseudozyma tsukubaensis strain 1E5, were confirmed to achieve an increased production of MEL as compared to the control. In particular, the strain transfected with the expression vector using E5Ptef showed a 1.8-fold increase in production amount as compared to the control, and a 1.5-fold increase as compared to the strain transfected with an expression vector using T34Pgap derived from Pseudozyma antarctica strain T-34.

8. Evaluation of Ability of Transformants to Consume the Starting Material Fat and Oil Each transformant was cultured with shaking in 2 mL of YM medium containing glycerol at 25° C. for 2 days to obtain a pre-culture liquid. Subsequently, 1 mL of the pre-culture liquid was inoculated into 20 mL of MEL medium containing 6% olive oil, and cultured with shaking at 25° C. for 7 days. On the second day of the culture, 6% olive oil was added; and on days 3, 4, 5, and 6, 3% olive oil was added (total amount of oil added: 24%). To the obtained cell culture liquid, an equal amount of ethyl acetate was added and stirred well. The ethyl acetate layer was then obtained by separation. The residual fat and oil in the ethyl acetate layer were quantified by using thin-layer chromatography (TLC) and high-performance liquid chromatography (HPLC) (FIG. 7(a) and (b)).

Figure 7:
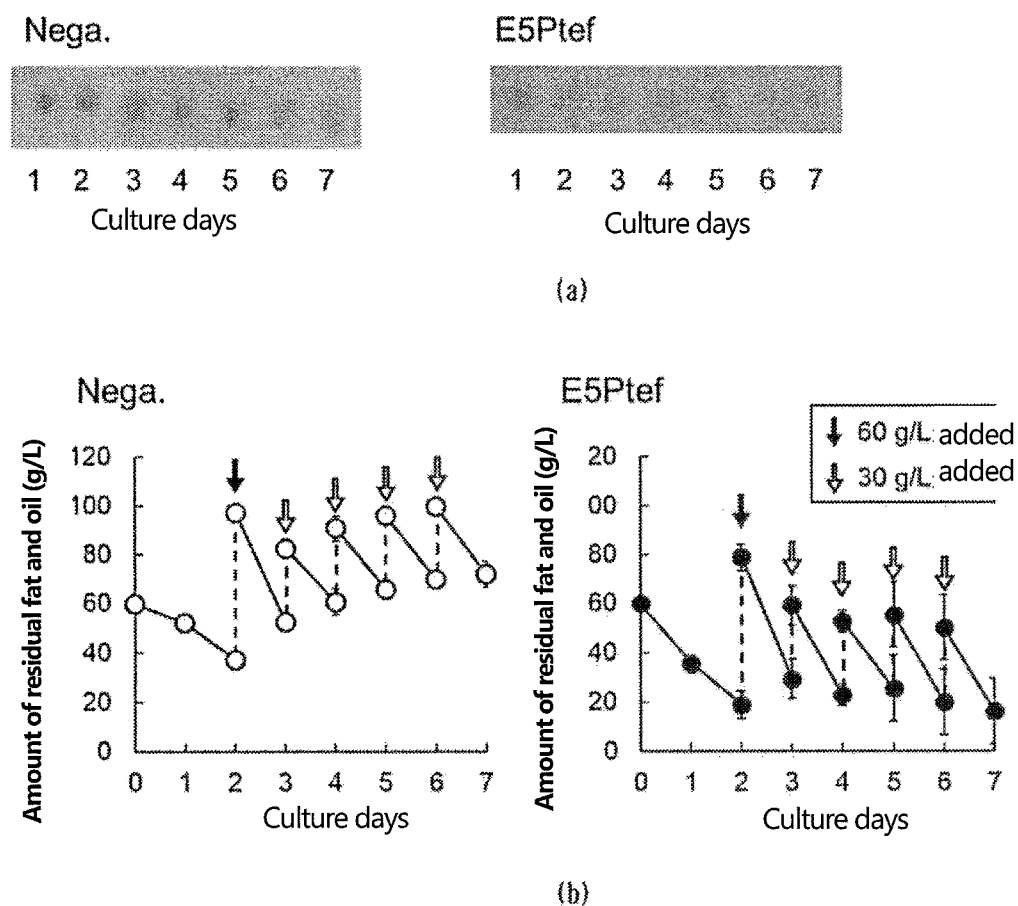
FIG. 7 shows the results of measuring the consumption of the starting material fat and oil by the exogenous lipase-transfected strains and the control by thin-layer chromatography (a) and HPLC (b).

As shown in FIG. 7, the strain transfected with the expression vector using E5Ptef derived from *Pseudozyma tsukubaensis* strain 1E5 was confirmed to have an increased amount of consumption of the starting material fat and oil as compared to the control. While the control degraded 168 g/L of fat and oil in 7 days, the strain transfected with the expression vector using E5Ptef was confirmed to degrade 224 g/L of fat and oil in 7 days, thus achieving a 1.3-fold increase in amount of consumption of fat and oil.

The wild-type 1E5 strain and the transformants (Nega and E5Ptef) prepared above in 4 were cultured with shaking in 100 mL of YM medium containing glycerol at 25° C. for 1 day to obtain pre-culture liquids. Subsequently, 60 mL of each pre-culture liquid was inoculated into a 6 L/10 L volume of MEL medium containing 15% olive oil, and cultured at 25° C. for 3 days. After the same amount of ethyl acetate was added to the resulting culture medium and stirred well, an ethyl acetate layer was obtained by separation. The MEL contained in the ethyl acetate layer was quantified by using high-performance liquid chromatography (HPLC). As for changes in amounts of the residual olive oil and fatty acids, the area ratios obtained by HPLC were measured.

Figure 11:
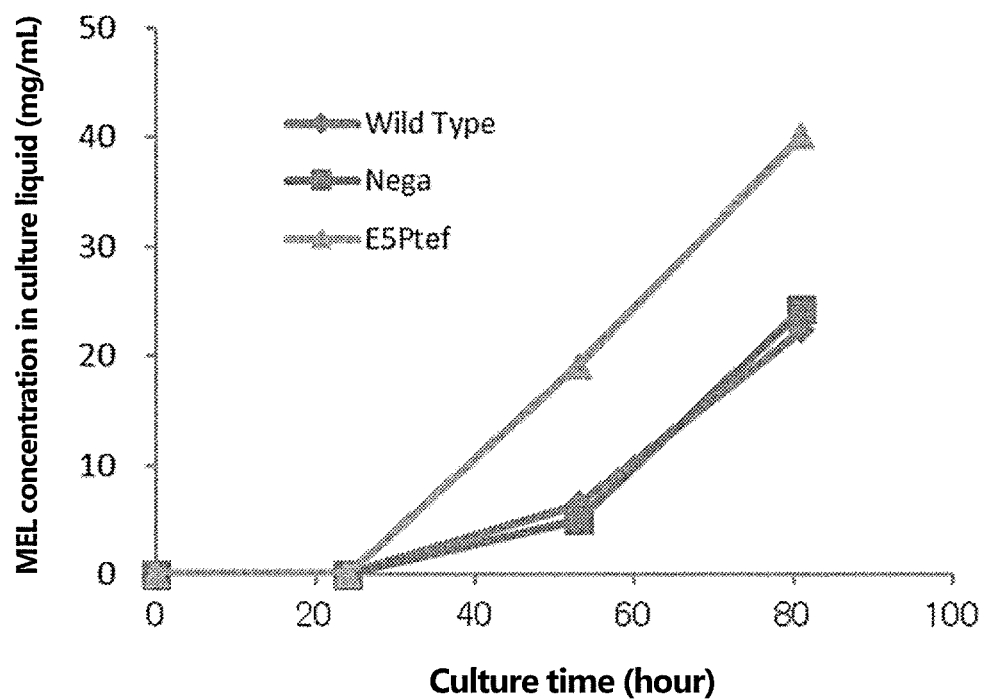
FIG. 11 shows the results of HPLC measurement of MEL production by an exogenous lipase-transfected strain and controls.
Figure 12:
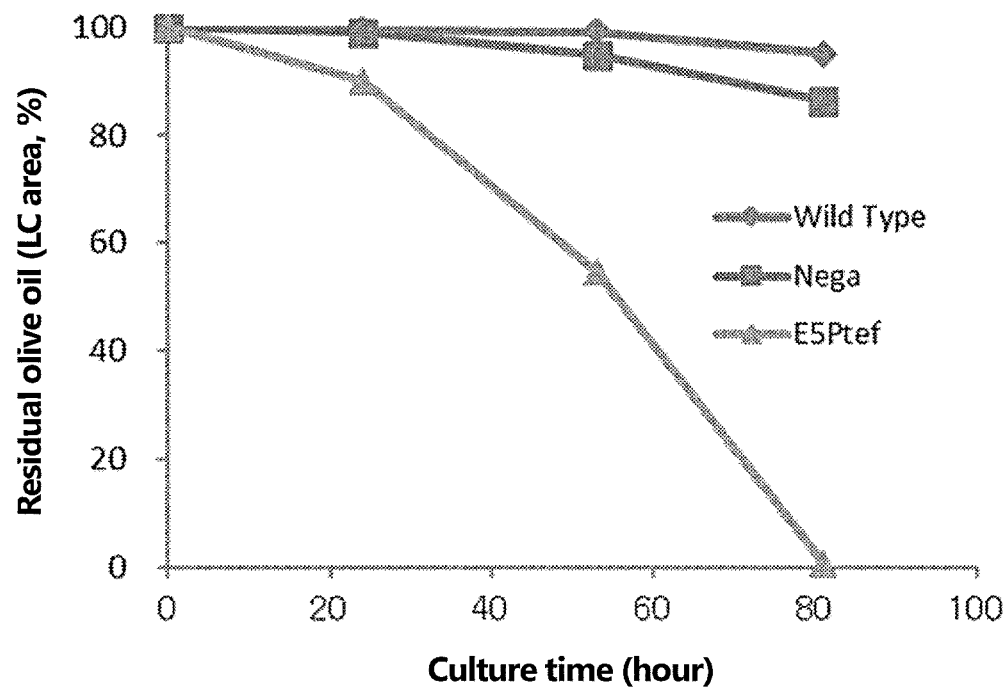
FIG. 12 shows the results of HPLC measurement of olive oil consumption by the exogenous lipase-transfected strain and the controls.
Figure 13:
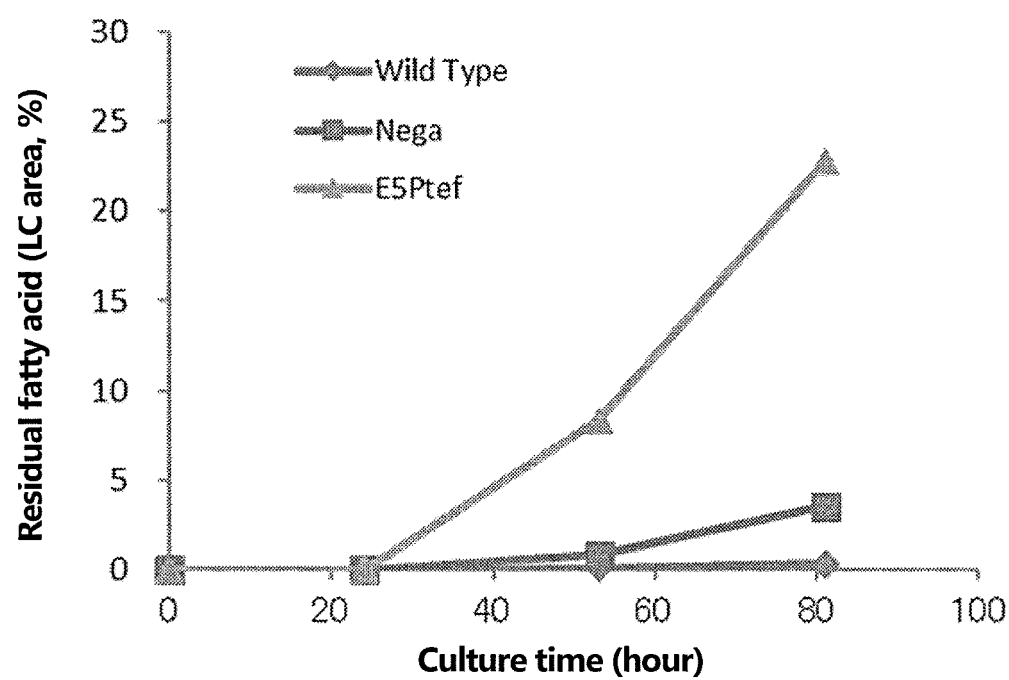
FIG. 13 shows the results of HPLC measurement of fatty acid production by the exogenous lipase-transfected strain and the controls.

As shown in FIG. 11, the strain transfected with the expression vector using an E5Ptef promoter showed higher MEL productivity than the wild-type strain and Nega strain. The percentage of the residual olive oil in the culture liquid, shown in FIG. 12, indicates that the strain transfected with E5Ptef degraded olive oil much faster than the wild-type strain or Nega strain. Further, as shown in FIG. 13, fatty acids are produced faster in the E5Ptef-transfected strain, as linked to the percentage of the residual olive oil shown in FIG. 12. These results show that the degradation of olive oil is accelerated in the E5Ptef-transformed strain, and fatty acids, which become a substrate of MEL, is quickly produced and MEL synthesis thus proceeds.

The invention claimed is:

1. A mannosylerythritol-lipid-producing microorganism transformed with an expression vector containing a gene that encodes a lipase under the control of E5Pgap promoter comprising the nucleotide sequence of SEQ ID NO: 1 or E5Ptef promoter comprising the nucleotide sequence of SEQ ID NO: 2, wherein the lipase comprises an amino acid sequence that is at least 80% identical to the amino acid sequence of any of SEQ ID NO: 5 to 13.

2. The mannosylerythritol-lipid-producing microorganism according to claim 1, wherein the mannosylerythritol-lipid-producing microorganism is a microorganism of the genus *Pseudozyma*.

3. The mannosylerythritol-lipid-producing microorganism according to claim 1, wherein the gene that encodes a lipase is derived from a microorganism of the genus *Pseudozyma*.

4. The mannosylerythritol-lipid-producing microorganism according to claim 1, wherein the mannosylerythritol-lipid-producing microorganism is *Pseudozyma tsukubaensis*.

5. An expression vector containing a gene that encodes a lipase under the control of E5Pgap promoter or E5Ptef promoter,
wherein the lipase comprises an amino acid sequence that is at least 80% identical to the amino acid sequence of any of SEQ ID NO: 5 to 13,
wherein the E5Pgap promoter comprises the nucleotide sequence of SEQ ID NO: 1, and
wherein the E5Ptef promoter comprises the nucleotide sequence of SEQ ID NO: 2.

6. The expression vector according to claim 5, wherein the gene that encodes a lipase is derived from a microorganism of the genus *Pseudozyma*.

7. The expression vector according to claim 5, which is an expression vector for transforming a mannosylerythritol-lipid-producing microorganism.

8. A method for producing a transformed mannosylerythritol-lipid-producing microorganism, the method comprising transforming a mannosylerythritol-lipid-producing microorganism with the expression vector of claim 5.

9. A method for producing a mannosylerythritol lipid using the mannosylerythritol-lipid-producing microorganism of claim 1.

10. A method for producing a mannosylerythritol lipid, the method comprising culturing the mannosylerythritol-lipid-producing microorganism of claim 1 in a medium containing a vegetable oil.

* * * * *

SEQUENCE LISTING

```
<160> NUMBER OF SEQ ID NOS: 32

<210> SEQ ID NO 1
<211> LENGTH: 1000
<212> TYPE: DNA
<213> ORGANISM: Pseudozyma tsukubaensis

<400> SEQUENCE: 1
ggagacatcc gctctctctt cagcctgagt aaaacctctt ccaccgtttc aacaagccgg      60
agcgctccat cgctttcacc cttccgccca tgtgttgttc tgtttgtgtg gagaagacgg     120
gcttgcacaa ctgaacacac gcagacccct ccgcttaagc ctcctttcag cagcctcgag     180
cgttgacagc cggctaatag atgcggagaa agagaaagca agtgagcaca gtgacgccaa     240
gacgcctggc gcctttgccg caagcagtgt tccttaccat ttgtattgag tcgcatcgcg     300
gaccctattc cctccggtat tgcgatacac agaaagcaga tcggctttgc tgtgaccgat     360
ctggttcttc tttcggccgc attgtgtctg cgcaatgact cgatggagag ccgcagtaaa     420
gctcaacaaa cgtgtgtgtg ttctgactga ttggtatcag cgaaagaccc accgaagaat     480
cagcgcggaa gatctctgag tgataagctt ttttctttgc ttgcagcaga gaagagggtg     540
caattaacac ctgccagaag atgggcacct tttctatttc gcgtcaaatt gaaatgcccg     600
atttggttgc atggtcactt cgaattgaaa cggtcaacgc tcggatcagg gtgtggagtt     660
gagctggatt tccagcagct tccttgcgcg gtgcagcgcg gtcaggccaa ctcgattttc     720
ggagtgattt tctgttcaga ttcaggaaga atggcagtca gagagagaag gaaagaggca     780
gatcgattgc tctcttgcgc ccgcatctgc cgctcactgt tgctgctgct gcatgttgat     840
cccggaaaga gtgcgcagag caactcactc agccagcctt cgtcggagag actcaaaggc     900
aaaagtatag caaaagcaca ttcaccatcg tcgctgttct tccttcctct ccaccatcga     960
atctttcgta tccatcccct catcccaaaa attattcaca                          1000
```

<210> SEQ ID NO 2
<211> LENGTH: 1000
<212> TYPE: DNA
<213> ORGANISM: Pseudozyma tsukubaensis

<400> SEQUENCE: 2

| | | | | | |
|---|---|---|---|---|---|
| tcgctcgaaa | taactcagca | catcgccctt | gcgctttgac | catccctgcc | cctcttgaat | 60 |
| tattactcaa | tcctccgatc | atagtcatag | cccgatgcag | atgccacgag | acaagcagaa | 120 |
| ctcgacaaca | tatagaaagc | ccagaagaag | gacgagaaga | tcttccggcg | gggcgatcaa | 180 |
| cgggagcttt | gcagacagct | ggagccgaag | aggaacgtgc | gcgggaaatg | tctgtcaata | 240 |
| ccttgtctga | cattggcaag | gtcttctgag | aagatacacg | cacagtccac | cttaggtctt | 300 |
| cagagcgttc | agagcgttca | gagcgttcag | actgttcaga | cagacagaga | cagctcttcc | 360 |
| cgtgggaacg | tagcgttaga | agggcgcatt | gcagcaattg | atctggtgct | aaaagtggct | 420 |
| gtatgcattt | gaattggagg | tgacttcact | ggcagtgcaa | agaacatttc | ctgaatacaa | 480 |
| gaaagctgca | aggaagcttt | ctgatgtgaa | gctctgtatt | gaaaattgtg | atccccaatt | 540 |
| tcaaatggct | gtatgcgctc | ttacacactg | tcggaatgcc | ttttgatcac | aaattgcaac | 600 |
| tcctggacgg | cgaaggcgct | cgttgaaaat | tcggtcttct | gattcgaaca | aagcgttgtg | 660 |
| ctgagctgtg | gtgggctgcc | cagtctggtg | caaagctcgc | tgtgcttctt | ccagattcaa | 720 |
| tgaggtctcg | agcctgccag | ttggtccaat | cattgaggca | cacaggcaga | ggaagctgga | 780 |
| agttgaccag | caagaaaaat | tttcttcgcc | tgtgagcggc | gacgagcaga | gatttgcccc | 840 |
| ccaaatcttc | gtttggcagg | cgtttgtgcg | acgcccgccc | gctcgtcgca | gtgtgcgcgc | 900 |
| cccagagcgc | caacagaata | aagaccgtct | gatctcgtca | aaatcttccc | ttcttccctc | 960 |
| atacatcgta | tcatatcata | catcaaaaac | atcatccaaa | | | 1000 |

<210> SEQ ID NO 3
<211> LENGTH: 1000
<212> TYPE: DNA
<213> ORGANISM: Pseudozyma  tsukubaensis

<400> SEQUENCE: 3

| | | | | | |
|---|---|---|---|---|---|
| cagcccttgt | tggaagatgg | gatggcgatg | gaggatgggg | atgagttgcc | agaggctgac | 60 |
| tttgctgctt | cgtacagtca | ctttagagat | gagcagaggg | gtggagagga | ggatgaggat | 120 |
| gcgtttgatt | tggatcttaa | ttgagagcgg | accaggcttg | aatgtaggcc | gttggcgttg | 180 |
| ttgcagtcgt | caaagtcaat | gagcgtcctc | aggtttagga | tcgcgaacgc | tactctcgcg | 240 |
| atggtttgga | atgacggctc | atagacgtta | tcacacatgc | tttacgttct | cactccctca | 300 |
| ttgtgtggaa | cttaatagac | atataccctt | ctgtcgtgct | gttcggagta | agatagcgat | 360 |
| ctttggcatg | ctcatggtac | ggcttctgcg | agtcaaaggg | tacacttcag | tgaaaacgat | 420 |
| cgcaatcaat | gggagttgtt | agaccggggt | cgtcaatctt | tgggaaaagt | aatttgaatt | 480 |
| atgagtcaaa | ttcgtgcgag | acattgacag | tgaccgacac | gtgactttga | ttcgaatttc | 540 |
| gcagttcttg | aatgccaaat | tttggcactc | attcgggcaa | ttgaccagtg | tcgttgcgaa | 600 |
| ggtaggagaa | gacaaggcag | cagggcgagg | aagaaatttg | actaacgccg | acagctcagc | 660 |
| caaggtcttc | tgagaggata | gatgacgtc | gcttgccgtt | cactcctttc | ttcttctcct | 720 |
| cacggtttca | agcagtaagt | atctcaactt | tttggtcgtg | agcgcacctc | gctcatcgat | 780 |
| cctctgatgg | cgtcgaacat | cacagcatca | cagcatccag | catcgatctg | tcaggacttg | 840 |
| atgatcgatg | ctcgtgctct | gttgcgcgtt | cactatcagg | cctttacagc | ctccgtctag | 900 |

```
atcagcacat actgacattg acgccatctc ttcttgctct tttcaactct caccatcgca    960
gaggacacca cctatctggt tagcaaaatc gtgactaaag                         1000
```

<210> SEQ ID NO 4
<211> LENGTH: 1000
<212> TYPE: DNA
<213> ORGANISM: Pseudozyma antarctica

<400> SEQUENCE: 4

```
tcgccagtcg cctcggaaag atccttctgg ctttccggat cgaacaacac agcgacggcc     60
ctccgcttgc acccgcatct ccacccgcac cccgcactag gctcatgcgc tcgtgctcct    120
ctctctttca cccgccaaat cggaagcagg cccacccgga gccctaccg gatgttttgc     180 attgtgtcga ggatgcaagg cggcggcggc ggtgagcggg ctgaagcgtg gtgacgccag    240
ccggcctccc cctgcctgtc tgccggtcgt gaagcctccc cctcttgcaa ctgctgctcg    300
gcttctcgcc cgacacgctt cactcggccg ttgctcatgg agctcagatc tgatcgacta    360
gcgcaccgca gcagacccaa caaatcagcg cccggtgata agaagaaagt gcagccaaaa    420
aaggtgaggg aaagtctcac cgagaaggag tcactgttgc gccgaagaaa gagcgagcag    480
gcagggtctt gcgaggcgca gctcagcaca cgcactgatc ttcaagtgat aacgcaaagg    540
ctccacatga ccctggaatt caagtgcttc gcgactttt tgaaatgcgg aatagatgtt     600
tttggatttc aggctggacg ctcggatcag cttgattggg cagtggagcc aagagcgatc    660
agcccgtgca tttccaaaag cttctgtggg agagcgcaga cagagtgggc attattcaga    720
agatcgattg ttcgcaaagc cgggaggggg gcagcagacc tgcgcggtca ccgcggcgca    780
ctccgggccc gtcagcagtc atcctttggc tcggctcgct ccgccactgg ctttgcgcag    840
aggccagcca gcggcagcag cgagcagtgt tgggcgacgc agaccccgcaa cctcctgcag    900 gcgcaaagcg atcaaaagtg cgtgtccgct tcgcctcttc ttccttctcc tccaccatcg    960
aatcttcttc gtgtcacact ccccatccat catctcaaaa                         1000
```

<210> SEQ ID NO 5
<211> LENGTH: 462
<212> TYPE: PRT
<213> ORGANISM: Pseudozyma antarctica

<400> SEQUENCE: 5

```
Met Arg Val Ser Leu Arg Ser Ile Thr Ser Leu Leu Ala Ala Ala Thr
  1               5                  10                  15

Ala Ala Val Leu Ala Ala Pro Ala Ala Glu Thr Leu Asp Arg Arg Ala
                 20                  25                  30

Ala Leu Pro Asn Pro Tyr Asp Asp Pro Phe Tyr Thr Thr Pro Ser Asn
             35                  40                  45

Ile Gly Thr Phe Ala Lys Gly Gln Val Ile Gln Ser Arg Lys Val Pro
         50                  55                  60

Thr Asp Ile Gly Asn Ala Asn Asn Ala Ala Ser Phe Gln Leu Gln Tyr
 65                  70                  75                  80

Arg Thr Thr Asn Thr Gln Asn Glu Ala Val Ala Asp Val Ala Thr Val
                 85                  90                  95

Trp Ile Pro Ala Lys Pro Ala Ser Pro Pro Lys Ile Phe Ser Tyr Gln
                100                 105                 110

Val Tyr Glu Asp Ala Thr Ala Leu Asp Cys Ala Pro Ser Tyr Ser Tyr
            115                 120                 125

Leu Thr Gly Leu Asp Gln Pro Asn Lys Val Thr Ala Val Leu Asp Thr
```

```
                130                 135                 140
Pro Ile Ile Ile Gly Trp Ala Leu Gln Gln Gly Tyr Tyr Val Val Ser
145                 150                 155                 160

Ser Asp His Glu Gly Phe Lys Ala Ala Phe Ile Ala Gly Tyr Glu Glu
                165                 170                 175

Gly Met Ala Ile Leu Asp Gly Ile Arg Ala Leu Lys Asn Tyr Gln Asn
                180                 185                 190

Leu Pro Ser Asp Ser Lys Val Ala Leu Glu Gly Tyr Ser Gly Gly Ala
                195                 200                 205

His Ala Thr Val Trp Ala Thr Ser Leu Ala Glu Ser Tyr Ala Pro Glu
                210                 215                 220

Leu Asn Ile Val Gly Ala Ser His Gly Gly Thr Pro Val Ser Ala Lys
225                 230                 235                 240

Asp Thr Phe Thr Phe Leu Asn Gly Gly Pro Phe Ala Gly Phe Ala Leu
                245                 250                 255

Ala Gly Val Ser Gly Leu Ser Leu Ala His Pro Asp Met Glu Ser Phe
                260                 265                 270

Ile Glu Ala Arg Leu Asn Ala Lys Gly Gln Gln Ala Leu Lys Gln Ile
                275                 280                 285

Arg Gly Arg Gly Phe Cys Leu Pro Gly Val Val Leu Thr Tyr Pro Phe
290                 295                 300

Leu Asn Val Phe Ser Leu Val Asn Asp Thr Asn Leu Leu Asn Glu Ala
305                 310                 315                 320

Pro Ile Val Ser Ile Leu Lys Gln Glu Thr Val Val Gln Ala Glu Ala
                325                 330                 335

Ser Tyr Thr Val Ser Val Pro Lys Phe Pro Arg Phe Ile Trp His Ala
                340                 345                 350

Val Pro Asp Glu Ile Val Pro Tyr Gln Pro Ala Ala Thr Tyr Val Lys
                355                 360                 365

Glu Gln Cys Ala Lys Gly Ala Asn Ile Asn Phe Ser Pro Tyr Pro Ile
                370                 375                 380

Ala Glu His Leu Thr Ala Glu Ile Phe Gly Leu Val Pro Ser Leu Trp
385                 390                 395                 400

Phe Ile Lys Gln Ala Phe Asp Gly Thr Thr Pro Lys Val Ile Cys Gly
                405                 410                 415

Thr Pro Ile Pro Ala Ile Ala Gly Ile Thr Thr Pro Ser Ala Asp Gln
                420                 425                 430

Val Leu Gly Ser Asp Leu Ala Asp Gln Leu Arg Ser Leu Asn Gly Lys
                435                 440                 445

Gln Ser Ala Phe Gly Lys Pro Phe Gly Pro Ile Thr Pro Pro
450                 455                 460

<210> SEQ ID NO 6
<211> LENGTH: 528
<212> TYPE: PRT
<213> ORGANISM: Pseudozyma aphidis

<400> SEQUENCE: 6

Met Arg His Arg Leu Asp Gly Ser Ile Val Gly Ser Ile Gly Ala Ala
1               5                   10                  15

Ile Ala Tyr Lys Gly Gln Pro Ser Ser Pro Gln Glu Tyr Ala Arg Ser
                20                  25                  30

Leu Lys Arg Leu His Ser Leu Ser Ser His Pro Ser Ser Ser Pro
                35                  40                  45
```

```
Arg Pro Glu Pro Tyr Pro Leu Ala Pro Leu Arg Leu Pro Pro Thr Phe
    50              55                  60
Arg Thr Met Arg Val Ser Leu Arg Ser Ile Thr Ser Leu Leu Ala Ala
65              70                  75                  80
Ala Thr Ala Ala Val Leu Ala Ala Pro Ala Thr Glu Thr Leu Asp Arg
                85                  90                  95
Arg Ala Ala Leu Pro Asn Pro Tyr Asp Asp Pro Phe Tyr Thr Thr Pro
            100                 105                 110
Ser Asn Ile Gly Thr Phe Ala Lys Gly Gln Val Ile Gln Ser Arg Lys
            115                 120                 125
Val Pro Thr Asp Ile Gly Asn Ala Asn Ala Ala Ser Phe Gln Leu
    130                 135                 140
Gln Tyr Arg Thr Thr Asn Thr Gln Asn Glu Ala Val Ala Asp Val Ala
145                 150                 155                 160
Thr Val Trp Ile Pro Ala Lys Pro Ala Ser Pro Pro Lys Ile Phe Ser
                165                 170                 175
Tyr Gln Val Tyr Glu Asp Ala Thr Ala Leu Asp Cys Ala Pro Ser Tyr
            180                 185                 190
Ser Tyr Leu Thr Gly Leu Asp Gln Pro Asn Lys Val Thr Ala Val Leu
        195                 200                 205
Asp Thr Pro Ile Ile Ile Gly Trp Ala Leu Gln Gln Gly Tyr Tyr Val
    210                 215                 220
Val Ser Ser Asp His Glu Gly Phe Lys Ala Ala Phe Ile Ala Gly Tyr
225                 230                 235                 240
Glu Glu Gly Met Ala Ile Leu Asp Gly Ile Arg Ala Leu Lys Asn Tyr
                245                 250                 255
Gln Asn Leu Pro Ser Asp Ser Lys Val Ala Leu Glu Gly Tyr Ser Gly
            260                 265                 270
Gly Ala His Ala Thr Val Trp Ala Thr Ser Leu Ala Asp Ser Tyr Ala
        275                 280                 285
Pro Glu Leu Asn Ile Val Gly Ala Ser His Gly Gly Thr Pro Val Ser
    290                 295                 300
Ala Lys Asp Thr Phe Thr Phe Leu Asn Gly Gly Pro Phe Ala Gly Phe
305                 310                 315                 320
Ala Leu Ala Gly Val Ser Gly Leu Ser Leu Ala His Pro Asp Met Glu
                325                 330                 335
Ser Phe Ile Glu Ala Arg Leu Asn Ala Lys Gly Gln Gln Thr Leu Lys
            340                 345                 350
Gln Ile Arg Gly Arg Gly Phe Cys Leu Pro Gln Val Val Leu Thr Tyr
        355                 360                 365
Pro Phe Leu Asn Val Phe Ser Leu Val Asn Asp Thr Asn Leu Leu Asn
    370                 375                 380
Glu Ala Pro Ile Ala Gly Ile Leu Lys Gln Glu Thr Val Val Gln Ala
385                 390                 395                 400
Glu Ala Ser Tyr Thr Val Ser Val Pro Lys Phe Pro Arg Phe Ile Trp
                405                 410                 415
His Ala Ile Pro Asp Glu Ile Val Pro Tyr Gln Pro Ala Ala Thr Tyr
            420                 425                 430
Val Lys Glu Gln Cys Ala Lys Gly Ala Asn Ile Asn Phe Ser Pro Tyr
        435                 440                 445
Pro Ile Ala Glu His Leu Thr Ala Glu Ile Phe Gly Leu Val Pro Ser
    450                 455                 460
Leu Trp Phe Ile Lys Gln Ala Phe Asp Gly Thr Thr Pro Lys Val Ile
```

```
            465                 470                 475                 480
Cys Gly Thr Pro Ile Pro Ala Ile Ala Gly Ile Thr Thr Pro Ser Ala
                485                 490                 495
Asp Gln Val Leu Gly Ser Asp Leu Ala Asn Gln Leu Arg Ser Leu Asn
                500                 505                 510
Gly Lys Gln Ser Ala Phe Gly Lys Pro Phe Gly Pro Ile Thr Pro Pro
                515                 520                 525
```

<210> SEQ ID NO 7
<211> LENGTH: 430
<212> TYPE: PRT
<213> ORGANISM: Pseudozyma hubeiensis

<400> SEQUENCE: 7

```
Met His Thr Arg Glu Thr Leu Pro Asp Pro Asn Asp Pro Phe Tyr
1               5                   10                  15
Ala Gln Pro Ser Asn Ile Ala Ser Tyr Ala Asn Gly Gln Val Ile Gln
                20                  25                  30
Ser Arg Lys Val Asp Thr Glu Ile Gly Ser Ile Asn Asn Val Asn Thr
            35                  40                  45
Phe Gln Val Lys Tyr Arg Thr Thr Asn Thr Gln Asn Gln Ala Gln Ser
    50                  55                  60
Asn Leu Ala Thr Val Trp Ile Pro Ser Lys Pro Ala Ser Pro Pro Lys
65                  70                  75                  80
Ile Phe Ser Tyr Gln Val Tyr Met Asp Ala Thr Gln Ile Asp Cys Ala
                85                  90                  95
Pro Ser Tyr Ser Tyr Val Thr Gly Leu Asp Lys Pro Gly Lys Gly Thr
                100                 105                 110
Val Ile Leu Asp Thr Pro Ile Val Ile Ser Trp Ala Leu Gln Gln Gly
            115                 120                 125
Tyr Tyr Val Val Ser Ser Asp Asp Glu Gly Pro Arg Ala Ala Phe Ile
    130                 135                 140
Ala Gly Tyr Glu Glu Gly Lys Ala Val Leu Asp Gly Ile Arg Ala Leu
145                 150                 155                 160
Gln Asn Tyr Ala Asn Leu Pro Lys Asp Ser Pro Ile Gly Met Tyr Gly
                165                 170                 175
Tyr Ser Gly Gly Ala His Thr Thr Gly Trp Ala Val Asn Leu Ala Gly
                180                 185                 190
Ser Tyr Ala Ser Glu Leu Asn Ile Ile Gly Ala Ala Tyr Gly Gly Leu
            195                 200                 205
Pro Ala Ser Ala Lys Asp Thr Phe Thr Phe Leu Asn Gly Lys Ser Ile
    210                 215                 220
Phe Ser Gly Phe Ala Leu Ala Gly Val Ser Gly Leu Ala Leu Gly His
225                 230                 235                 240
Pro Asp Met Glu Ala Phe Ile Lys Pro Arg Leu Asn Ala Lys Gly Asn
                245                 250                 255
Gln Thr Leu Ala Gln Ile Arg Ser Arg Gly Glu Cys Ile Gly Gln Val
                260                 265                 270
Ala Leu Gly Tyr Pro Phe Leu Asp Val Phe Ser Leu Val Asn Asp Thr
            275                 280                 285
Asn Leu Leu Asn Glu Glu Pro Ile Val Ser Ile Leu Lys Thr Glu Thr
    290                 295                 300
Leu Val Gln Ala Glu Ala Ser Tyr Thr Val Pro Val Pro Lys Phe Pro
305                 310                 315                 320
```

Arg Phe Met Trp His Ala Leu Pro Asp Glu Ile Val Pro Phe Gln Pro
                325                 330                 335

Ala Gln Asp Tyr Val Thr Glu Gln Cys Ala Lys Gly Ala Asp Ile Asn
            340                 345                 350

Trp Asn Val Tyr Pro Ile Ala Glu His Ile Ser Ala Glu Leu Leu Gly
        355                 360                 365

Leu Leu Pro Gly Ile Asp Trp Leu Ser Lys Ala Tyr Lys Gly Gln Ala
370                 375                 380

Pro Lys Val Ala Cys Gly Gly Val Pro Ala Thr Pro Pro Ala
385                 390                 395                 400

Glu Asp Val Leu Gly Gly Asp Leu Ala Ser Gln Phe Arg Ser Leu Asn
                405                 410                 415

Gly Lys Gln Ser Ala Tyr Gly Lys Pro Phe Asn Ala Gly Phe
            420                 425                 430

<210> SEQ ID NO 8
<211> LENGTH: 458
<212> TYPE: PRT
<213> ORGANISM: Ustilago hordei

<400> SEQUENCE: 8

Met Arg Phe Phe Leu Gly Ala Val Leu Ala Leu Ala Ala Ala Ala Ile
1               5                   10                  15

Ala Ala Leu Ala Val Pro Met Glu Arg Arg Ala Gln Phe Pro Asp Pro
            20                  25                  30

Asn Glu Asp Pro Phe Tyr Gln Gln Pro Ser Asn Val Ala Thr Tyr Ala
        35                  40                  45

Asn Gly Gln Ile Ile Arg Ser Arg Lys Ala Asp Thr Asp Ile Gly Asn
50                  55                  60

Ser Asn Lys Ala Gln Ala Phe Gln Leu Ser Tyr Arg Thr Thr Asn Thr
65                  70                  75                  80

Gln Gln Gln Ala Gln Ala Asn Val Ala Thr Val Trp Ile Pro Ala Lys
                85                  90                  95

Pro Ala Ser Pro Pro Lys Ile Phe Ser Tyr Gln Val Tyr Glu Asp Ser
            100                 105                 110

Thr Gln Leu Asp Cys Ala Pro Ser Tyr Ser Tyr Leu Ala Gly Phe Asp
        115                 120                 125

Pro Pro Asn Lys Ala Thr Thr Ile Leu Asp Thr Ser Leu Ile Ile Gly
130                 135                 140

Trp Ala Leu Gln Gln Gly Tyr Tyr Val Leu Ser Ser Asp His Glu Gly
145                 150                 155                 160

Pro Arg Ala Ala Phe Ile Ala Gly Tyr Glu Glu Gly Met Ala Ile Leu
                165                 170                 175

Asp Ala Ile Arg Ala Leu Gln Asn Phe Arg His Leu Pro Lys Asp Ser
            180                 185                 190

Pro Val Gly Met Tyr Gly Tyr Ser Gly Gly Ala His Ala Thr Val Trp
        195                 200                 205

Ala Glu Ser Leu Ala Gly Ser Tyr Ala Pro Glu Ile Asn Ile Ile Ala
210                 215                 220

Thr Ala His Gly Gly Thr Pro Phe Ser Thr Lys Asp Thr Phe Thr Phe
225                 230                 235                 240

Ile Asn Gly Gly Val Phe Ala Gly Phe Ala Ile Ala Gly Val Ser Gly
                245                 250                 255

Leu Ala Leu Val His Pro Ala Met Gln Ala Tyr Ile Lys Pro Arg Leu
            260                 265                 270

```
Asn Ala Gln Gly Val Lys Val Phe Gln Gln Ile Arg Ser Arg Ala Phe
            275                 280                 285

Cys Ile Ala Gln Val Val Phe Thr Tyr Pro Phe Thr Asn Val Phe Asn
        290                 295                 300

Leu Val Asn Gly Thr Asp Leu Leu Asn Gln Glu Pro Ile Arg Ser Ile
305                 310                 315                 320

Leu Lys Arg Glu Thr Leu Val Gln Ser Glu Ala Ser Cys Asp Val Pro
                325                 330                 335

Val Val Arg Ala Pro Arg Phe Ile Trp His Ala Ala Leu Asp Glu Ile
            340                 345                 350

Val Pro Tyr Ala Pro Ala Ala Gln Tyr Val Lys Glu Gln Cys Asp Lys
        355                 360                 365

Gly Ala Gln Ile His Phe Glu Thr Tyr Pro Ile Ala Glu His Phe Ser
370                 375                 380

Ala Glu Phe Phe Gly Leu Val Pro Ala Leu Trp Phe Leu Ser Gln Ala
385                 390                 395                 400

Tyr Ala Gly Lys Ala Ala Lys Thr Val Cys Gly Thr Ser Ile Pro Ala
                405                 410                 415

Ile Pro Gly Phe Thr Val Pro Ser Ala Glu Glu Val Leu Gly Ala Asp
            420                 425                 430

Leu Ala Lys Gln Leu Lys Gly Leu Ser Ala Lys Asp Leu Ser Ala Lys
        435                 440                 445

Asp Leu Ser Gly Lys His Leu Pro Ala Leu
450                 455

<210> SEQ ID NO 9
<211> LENGTH: 458
<212> TYPE: PRT
<213> ORGANISM: Ustilago maydis

<400> SEQUENCE: 9

Met Arg Phe Ile Ala Val Arg Ala Ile Val Thr Leu Ala Ala Ala Ala
1               5                   10                  15

Ala Val Ser Leu Ala Val Pro Thr Glu Arg Arg Ala Ala Phe Ala Asp
            20                  25                  30

Pro Asn Asp Asp Leu Phe Tyr Thr Thr Pro Asp Asn Ile Asn Thr Tyr
        35                  40                  45

Ala Asn Gly Gln Val Ile Gln Ser Arg Lys Ala Asp Thr Asp Ile Gly
    50                  55                  60

Asn Ser Asn Lys Val Glu Ala Phe Gln Leu Gln Tyr Arg Thr Thr Asn
65                  70                  75                  80

Thr Gln Lys Glu Ala Gln Ala Asn Val Ala Thr Val Trp Ile Pro Asn
                85                  90                  95

Lys Pro Ala Ser Pro Pro Lys Ile Phe Ser Tyr Gln Val Tyr Gln Asp
            100                 105                 110

Ser Thr Gln Leu Asn Cys Ala Pro Ser Tyr Ser Phe Leu Lys Gly Leu
        115                 120                 125

Asp Lys Pro Asn Lys Ala Thr Thr Ile Leu Glu Ala Pro Ile Ile Ile
    130                 135                 140

Gly Trp Ala Leu Gln Gln Gly Phe Tyr Val Val Ser Ser Asp His Glu
145                 150                 155                 160

Gly Pro Arg Ser Ser Phe Ile Ala Gly Tyr Glu Glu Gly Met Ala Ile
                165                 170                 175

Leu Asp Gly Ile Arg Ala Leu Lys Asn Tyr Ala Lys Leu Pro Thr Asp
```

```
            180                 185                 190
Ser Ala Ile Gly Phe Tyr Gly Tyr Ser Gly Gly Ala His Ala Thr Gly
            195                 200                 205

Trp Ala Ala Asn Leu Ala Gly Ser Tyr Ala Pro Glu His Asn Ile Ile
            210                 215                 220

Gly Ala Ala Tyr Gly Gly Leu Pro Ala Ser Ala Arg Asp Thr Phe Asn
225                 230                 235                 240

Phe Leu Asn Lys Gly Ala Phe Gly Phe Ala Ile Ala Gly Val Ser
                245                 250                 255

Gly Leu Ala Leu Ala Tyr Pro Asp Val Glu Thr Tyr Ile Gln Ser Arg
            260                 265                 270

Leu Asn Ala Lys Gly Glu Lys Val Phe Lys Gln Val Arg Ser Arg Gly
            275                 280                 285

Phe Cys Ile Gly Gln Val Val Leu Thr Tyr Pro Phe Val Asp Ala Tyr
            290                 295                 300

Ser Leu Ile Asn Asp Thr Asn Leu Leu Asn Glu Glu Pro Val Ala Ser
305                 310                 315                 320

Thr Leu Lys Ser Glu Thr Leu Val Gln Ala Glu Ala Ser Tyr Thr Val
                325                 330                 335

Pro Val Pro Lys Phe Pro Arg Phe Ile Trp His Ala Leu Leu Asp Glu
            340                 345                 350

Ile Val Pro Phe His Ser Ala Ala Thr Tyr Val Lys Glu Gln Cys Ser
            355                 360                 365

Lys Gly Ala Asp Ile Asn Trp Asn Val Tyr Ser Phe Ala Glu His Ile
            370                 375                 380

Ser Ala Glu Leu Phe Gly Leu Leu Pro Gly Leu Asp Trp Leu Asn Lys
385                 390                 395                 400

Ala Tyr Lys Gly Gln Ala Pro Lys Val Pro Cys Gly Gly Gly Ala Gln
                405                 410                 415

Ser Val Met Gly Ala Ser Gly Pro Pro Ala Gln Asp Val Leu Gly Ala
            420                 425                 430

Asp Leu Ala Ser Gln Leu Arg Ser Leu Gln Gly Lys Pro Ser Ala Phe
            435                 440                 445

Gly Asn Lys Pro Phe Gly Ser Ile Ser Pro
            450                 455

<210> SEQ ID NO 10
<211> LENGTH: 459
<212> TYPE: PRT
<213> ORGANISM: Sporisorium reilianum

<400> SEQUENCE: 10

Met Arg Phe Phe Ala Gln Thr Leu Val Ala Leu Ala Ala Ala Thr
1               5                   10                  15

Val Ser Leu Ala Ala Pro Leu Glu Arg Arg Ala Gln Phe Pro Asp Pro
            20                  25                  30

Asn Asp Asp Pro Phe Tyr Ser Ala Pro Ala Asn Ile Gly Ser Tyr Val
            35                  40                  45

Asn Gly Gln Val Ile Gln Ser Arg Ser Ala Thr Thr Asp Ile Gly Thr
        50                  55                  60

Ser Asn Asn Ala Ala Ser Phe Gln Leu Leu Tyr Arg Thr Thr Asn Thr
65              70                  75                  80

Ser Asn Leu Pro Glu Ala Thr Val Ala Thr Val Trp Ile Pro Ala Lys
                85                  90                  95
```

-continued

```
Pro Ala Ser Pro Pro Lys Ile Phe Ser Tyr Gln Val Tyr Glu Asp Ala
            100                 105                 110

Thr Gln Leu Asn Cys Ala Pro Ser Tyr Ser Tyr Leu Ser Gly Leu Asp
        115                 120                 125

Glu Pro Gly Lys Gly Thr Val Ile Leu Asp Thr Pro Ile Val Ile Ser
    130                 135                 140

Trp Ala Leu Gln Gln Gly Tyr Tyr Val Val Ser Ala Asp His Glu Gly
145                 150                 155                 160

Pro Lys Ala Ala Phe Ile Ala Gly Cys Gln Glu Gly Arg Ala Ile Leu
                165                 170                 175

Asp Gly Val Arg Ala Leu Arg Asn Phe Gln Asn Leu Ala Ser Asn Ser
            180                 185                 190

Ala Val Gly Phe Tyr Gly Tyr Ser Gly Gly Gly His Ala Thr Gly Trp
        195                 200                 205

Ala Val Ser Leu Ala Gly Ser Tyr Ala Pro Asp Val Asn Ile Ile Gly
    210                 215                 220

Ala Ala Tyr Gly Gly Val Pro Thr Ser Thr Arg Asp Ile Phe Asn Phe
225                 230                 235                 240

Leu Asn Gly Gly Ala Phe Ala Gly Phe Ala Val Ala Gly Val Ser Gly
                245                 250                 255

Leu Gly Leu Ala Tyr Pro Glu Leu Glu Ala Tyr Ile Glu Pro Arg Leu
            260                 265                 270

Asn Ala Lys Gly Gln Asp Ala Leu Lys Arg Phe Arg Ser Arg Gly Tyr
        275                 280                 285

Cys Ile Gly Gln Val Val Thr Ser Glu Asn Phe Val Asp Ile Tyr Thr
    290                 295                 300

Leu Val Asn Asp Ser Asn Ile Leu Asn Glu Pro Ile Pro Ser Gln Val
305                 310                 315                 320

Leu Ala Lys Glu Thr Leu Leu Gln Thr Gln Ala Ser Tyr Thr Val Pro
                325                 330                 335

Val Pro Lys Ser Pro Arg Phe Ile Trp His Ala Leu Glu Asp Glu Ile
            340                 345                 350

Val Pro Phe Lys Pro Ala Gln Gln Tyr Val Thr Glu Gln Cys Ala Lys
        355                 360                 365

Gly Ala Asn Ile Asn Trp Asn Val Phe Pro Ile Ala Glu His Ile Ser
    370                 375                 380

Ala Glu Leu Phe Gly Leu Val Pro Gly Leu Asp Trp Leu Ser Lys Ala
385                 390                 395                 400

Tyr Arg Gly Gln Ala Pro Lys Val Ile Cys Gly Ser Ser Ile Pro Ala
                405                 410                 415

Ile Thr Gly Val Asn Ser Pro Ser Ala Gln Gln Val Leu Gly Ala Asp
            420                 425                 430

Leu Ala Gln Gln Leu Ser Asn Leu Asn Gly Lys Gln Ser Ala Phe Gly
        435                 440                 445

Lys Pro Tyr Gly Pro Ile Thr Pro Pro Thr Ala
    450                 455

<210> SEQ ID NO 11
<211> LENGTH: 459
<212> TYPE: PRT
<213> ORGANISM: Sporisorium scitamineum

<400> SEQUENCE: 11

Met Lys Phe Phe Pro Gln Ala Val Val Ala Leu Ala Ala Ala Ala Thr
1               5                   10                  15
```

```
Ala Ala Leu Ala Val Pro Met Gln Lys Arg Ala Gln Tyr Pro Asp Pro
             20                  25                  30

Asn Asp Asp Pro Phe Tyr Ser Val Pro Ala Asn Ile Gly Ser Tyr Ser
         35                  40                  45

Asn Gly Gln Val Ile Gln Ser Arg Ser Ala Thr Thr Asp Ile Gly Asn
 50                  55                  60

Ala Asn Asn Ala Leu Ser Phe Gln Leu Leu Tyr Arg Thr Thr Asn Thr
 65                  70                  75                  80

Ser Asn Gln Ala Asp Ala Thr Val Ala Thr Val Trp Ile Pro Ala Lys
                 85                  90                  95

Pro Ala Ser Pro Pro Lys Ile Phe Ser Tyr Gln Val Tyr Glu Asp Ala
            100                 105                 110

Thr Gln Leu Asp Cys Ala Pro Ser Tyr Asn Tyr Leu Ser Gly Leu Glu
            115                 120                 125

Gln Pro Gly Lys Ala Thr Val Ile Leu Asp Thr Pro Ile Ile Ile Gly
130                 135                 140

Trp Ala Leu Gln Gln Gly Tyr Tyr Val Val Ser Ala Asp His Glu Gly
145                 150                 155                 160

Pro Lys Ala Ala Phe Ile Ala Gly Tyr Gln Glu Gly Arg Ala Ile Leu
                165                 170                 175

Asp Gly Ile Arg Ala Leu Arg Asn Phe Lys Asp Leu Pro Ser Ser Ser
            180                 185                 190

Ala Val Gly Phe Tyr Gly Tyr Ser Gly Gly His Ala Thr Gly Trp
            195                 200                 205

Ala Val Asn Leu Ala Asp Ser Tyr Ala Pro Asp Val Asn Ile Ile Gly
            210                 215                 220

Ala Ala Tyr Gly Gly Leu Pro Ala Ser Thr Arg Asp Ile Phe Asn Phe
225                 230                 235                 240

Leu Asn Gly Gly Val Phe Ala Gly Phe Ala Val Ala Gly Val Ser Gly
                245                 250                 255

Leu Gly Gln Ala Tyr Pro Glu Leu Glu Ala Phe Val Glu Pro Arg Leu
            260                 265                 270

Asn Ala Lys Gly Gln Glu Ala Leu Lys Lys Phe Arg Ser Arg Gly Phe
            275                 280                 285

Cys Ile Gly Gln Val Val Thr Asn Glu Asn Phe Val Asp Ile Tyr Thr
290                 295                 300

Leu Val Asn Asp Ser Asn Ile Leu Asn Gln Pro Ile Pro Ser Glu Val
305                 310                 315                 320

Leu Ala Lys Glu Thr Leu Leu Gln Ser Gln Ala Ser Tyr Thr Val Pro
                325                 330                 335

Val Pro Lys Phe Pro Arg Phe Ile Trp His Ala Leu Glu Asp Glu Ile
            340                 345                 350

Val Pro Phe Ile Pro Ala Gln Lys Tyr Val Gln Glu Gln Cys Ala Lys
            355                 360                 365

Gly Ala Asn Ile Asn Trp Asn Val Phe Pro Ile Ala Glu His Leu Thr
370                 375                 380

Ala Glu Ile Phe Gly Leu Val Pro Gly Leu Tyr Trp Leu Ser Gln Ala
385                 390                 395                 400

Tyr Ala Gly Lys Ala Pro Lys Val Thr Cys Gly Gly Thr Pro Ala
                405                 410                 415

Ile Thr Gly Val Thr Ser Pro Ser Ala Gln Gln Val Leu Gly Ala Asp
            420                 425                 430
```

Leu Ala Lys Gln Leu Ser Ser Leu Asn Gly Lys Gln Ser Ala Phe Gly
            435                 440                 445

Lys Pro Phe Gly Ser Ile Thr Pro Pro Thr Ser
    450                 455

<210> SEQ ID NO 12
<211> LENGTH: 457
<212> TYPE: PRT
<213> ORGANISM: MELanopsichium pennsylvanicum

<400> SEQUENCE: 12

Met Arg Phe Phe Ser Arg Ala Val Ile Gly Leu Ala Ala Val Ala Thr
1               5                   10                  15

Ala Ala Ile Ala Met Pro Thr His Lys Arg Ala Ala Phe Pro Asp Pro
            20                  25                  30

Asn Asp Asp Ser Phe Tyr Gln Asn Pro Ala Asn Ile Ala Thr Tyr Ala
        35                  40                  45

Asn Gly Gln Ile Ile Gln Ser Arg Asn Val Val Thr Asp Ile Gly Asn
    50                  55                  60

Asn Asn Lys Ala Asp Ser Phe Gln Leu Ser Tyr Arg Thr Thr Asn Thr
65                  70                  75                  80

Gln Lys Asp Ala Val Ala Asn Val Ala Thr Ile Phe Ile Pro Ser Lys
                85                  90                  95

Pro Ala Ser Pro Pro Lys Ile Phe Ser Tyr Gln Val Tyr Glu Asp Ser
            100                 105                 110

Thr Gln Leu Asn Cys Ala Pro Ser Tyr Asn Tyr Leu Thr Gly Phe Asp
        115                 120                 125

Glu Pro Asn Lys Val Thr Thr Ser Leu Asp Thr Pro Ile Ile Ile Ser
    130                 135                 140

Trp Ala Leu Asn Gln Gly Tyr Tyr Val Val Ser Ser Asp Ala Glu Gly
145                 150                 155                 160

Gln Arg Ser Ala Phe Ile Ala Gly Tyr Glu Glu Gly Met Ala Ile Leu
                165                 170                 175

Asp Ala Ile Arg Ala Leu Lys Asn Tyr Lys Ser Leu Pro Lys Asp Thr
            180                 185                 190

Glu Thr Ala Leu Tyr Gly Tyr Ser Gly Gly Ala His Ala Thr Ala Trp
        195                 200                 205

Ala Val Ser Leu Ser Ala Ser Tyr Ala Pro Asp Ile Asn Ile Ile Gly
    210                 215                 220

Ala Ala Tyr Gly Gly Thr Pro Thr Ser Ala Lys Asp Thr Phe Asn Tyr
225                 230                 235                 240

Leu Asn Lys Gly Leu Phe Ala Gly Phe Ala Val Ser Gly Val Ser Gly
                245                 250                 255

Leu Ala Leu Ala His Pro Asp Met Glu Ser Phe Ile Glu Pro Arg Leu
            260                 265                 270

Asn Ala Val Gly Gln Gln Val Phe Gln Lys Val Arg Ser Arg Gly Tyr
        275                 280                 285

Cys Ile Val Gln Val Ser Thr Asn Asn Leu Arg Asp Val Tyr Thr
    290                 295                 300

Leu Val Asn Asp Thr Asn Leu Leu Asn Glu Glu Pro Ile Lys Ser Ile
305                 310                 315                 320

Leu Ala Leu Glu Thr Leu Val Gln Ala Glu Ala Ser Tyr Thr Val Pro
                325                 330                 335

Val Pro Lys Phe Pro Arg Phe Met Trp His Ala Leu Pro Asp Glu Ile
            340                 345                 350

-continued

Val Pro Phe Gln Pro Ala Ala Asp Tyr Val Gln Glu Gln Cys Ser Lys
            355                 360                 365

Gly Ala Asn Ile Asn Trp Asn Val Tyr Pro Ile Ala Glu His Val Thr
    370                 375                 380

Ala Glu Ile Phe Gly Ile Ile Pro Ala Leu Asp Trp Leu Gly Lys Val
385                 390                 395                 400

Tyr Ser Gly Asn Ala Pro Lys Val Ala Cys Gly Gly Val Pro Gly
                405                 410                 415

Ile Ala Gly Val Thr Thr Pro Pro Ala Asn Asp Val Leu Gly Ser Ala
                420                 425                 430

Leu Ala Gln Gln Leu Gly Asn Leu Ser Gly Lys Thr Ser Ala Phe Gly
            435                 440                 445

Lys Pro Phe Gly Thr Ile Thr Pro Ser
            450                 455

<210> SEQ ID NO 13
<211> LENGTH: 458
<212> TYPE: PRT
<213> ORGANISM: Kurtzmanomyces

<400> SEQUENCE: 13

Met Arg Phe Phe Leu Arg Ala Val Leu Gly Leu Ala Val Thr Ala Thr
1               5                   10                  15

Ala Ala Leu Ala Ala Pro Leu Glu Pro Arg Ala Ala Leu Pro Asp Pro
            20                  25                  30

Asn Glu Asp Pro Phe Tyr Ser Thr Pro Ser Asn Ile Glu Thr Phe Ala
        35                  40                  45

Asn Gly Gln Ile Ile Gln Ser Arg Lys Val Pro Thr Asp Ile Gly Asn
    50                  55                  60

Ser Asn Asn Ala Ala Ser Tyr Gln Leu Ser Tyr Arg Thr Thr Asn Thr
65                  70                  75                  80

Gln Glu Asp Ala Val Ala Asn Val Ala Thr Ile Trp Ile Pro Ala Lys
                85                  90                  95

Pro Ser Pro Pro Arg Ile Phe Thr Tyr Gln Val Tyr Glu Asp Ser
            100                 105                 110

Thr Gln Leu Asp Cys Ala Pro Ser Tyr Ser Tyr Leu Thr Gly Tyr Asp
        115                 120                 125

Gln Pro Asn Lys Ala Thr Ala Val Leu Asp Thr Pro Ile Val Ile Ser
    130                 135                 140

Trp Ala Leu Gln Gln Gly Tyr Tyr Val Val Ser Ala Asp His Glu Gly
145                 150                 155                 160

Ala Arg Ser Ala Phe Ile Ala Gly Tyr Glu Glu Gly Met Ala Ala Leu
                165                 170                 175

Asp Gly Ile Arg Ala Leu Arg Asn Tyr Ala Lys Leu Pro Gln Asp Ser
            180                 185                 190

Ala Val Gly Ala Tyr Gly Tyr Ser Gly Gly Ala His Ala Thr Val Trp
        195                 200                 205

Ala Thr Ser Leu Ala Ala Ala Tyr Ala Pro Glu Ile Asn Phe Ile Gly
    210                 215                 220

Ala Ala His Gly Gly Thr Pro Val Ser Ala Lys Asp Thr Phe Thr Phe
225                 230                 235                 240

Ile Asn Gly Gly Phe Phe Ala Gly Phe Ala Ile Ala Gly Val Ser Gly
                245                 250                 255

Leu Ala Asn Ala His Pro Asp Met Glu Ala Phe Ile Gln Pro Arg Leu

-continued

```
                260                 265                 270
Asn Ala Glu Gly Val Lys Thr Leu Lys Gln Ile Arg Ser Arg Gly Phe
                275                 280                 285

Cys Leu Pro Glu Val Val Thr Thr Tyr Pro Phe Lys Asn Val Phe Ala
                290                 295                 300

Leu Val Asn Asp Thr Asn Leu Leu Thr Glu Gln Pro Ile Ser Gly Ile
305                 310                 315                 320

Leu Gln Gln Glu Thr Leu Val Gln Ser Glu Ala Ser Tyr Ala Val Pro
                325                 330                 335

Val Pro Lys Phe Pro Arg Phe Leu Trp His Ala Ala Leu Asp Glu Ile
                340                 345                 350

Val Pro Tyr Val Pro Val Thr Glu Tyr Val Lys Glu Gln Cys Ala Lys
                355                 360                 365

Gly Ala Asn Ile Asn Phe Asn Thr Tyr Pro Ile Ala Glu His Leu Thr
                370                 375                 380

Ala Glu Ile Phe Gly Leu Val Pro Gly Leu Trp Phe Leu Ser Gln Ala
385                 390                 395                 400

Tyr Glu Gly Lys Ala Pro Ala Val Gln Cys Gly Thr Ala Leu Pro Ala
                405                 410                 415

Ala Pro Ser Ala Gln Gln Val Leu Gly Asn Asp Leu Ala Asn Gln Leu
                420                 425                 430

Ser Ser Leu Asn Gly Lys Gln Ser Pro Phe Gly Lys Pro Phe Gly Pro
                435                 440                 445

Ile Ser Pro Thr Ser Leu Asp Lys Leu Leu
450                 455
```

<210> SEQ ID NO 14
<211> LENGTH: 1389
<212> TYPE: DNA
<213> ORGANISM: Pseudozyma antarctica

<400> SEQUENCE: 14

```
atgcgagtgt ccttgcgctc cattacctcg ctgctggcgg cggcaacggc agctgtgctc      60
gcggctccgg cggccgagac gctggaccga cgggcggcgc tgcccaaccc ctacgacgat     120
cccttctaca cgacgccatc caacatcggc acgtttgcca agggccaggt gatccaatct     180
cgcaaggtgc ccacggacat cggcaacgcc aacaacgctg cgtcgttcca gctgcagtac     240
cgcaccacca acacgcagaa cgaggcggtg ccgacgtggc caccgtgtgt gatcccggcc     300
aagcccgctt cgccgcccaa gatcttttcg taccaggtct acgaggatgc cacggcgctc     360
gactgtgctc cgagctacag ctacctcact ggattggacc agccgaacaa ggtgacggcg     420
gtgctcgaca cgcccatcat catcggctgg gcgctgcagc agggctacta cgtcgtctcg     480
tccgaccacg aaggcttcaa agccgccttc atcgctggct acgaagaggg catggctatc     540
ctcgacggca tccgcgcgct caagaactac cagaacctgc catccgacag caaggtcgct     600
cttgagggct acagtggcgg agctcacgcc accgtgtggg cgacttcgct cgctgaatcg     660
tacgcgcccg agctcaacat tgtcggtgct tcgcacggcg gcacgcccgt gagcgccaag     720
gacaccttca cattcctcaa cggcggaccc ttcgccggct tgccctggc aggtgtttcg      780
ggtctctcgc tcgctcatcc tgacatggag agcttcattg aggcccgatt gaacgccaag     840
ggtcagcagg cgctcaagca gatccgcggc gtggcttct gcctgcctgg ggtggtgttg      900
acctaccccct cctcaacgt cttctcgctg gtcaacgaca cgaacctgct gaatgaggcg     960
ccgatcgtta gcatcctcaa gcaggagacg gtggtccagg ccgaagcgag ctacacagtg    1020
```

-continued

```
tcggtgccca agttcccgcg cttcatctgg catgcggtcc ccgacgagat cgtgccgtac    1080
cagcctgccg ctacctacgt caaggagcaa tgtgccaagg gcgccaacat caacttttcg    1140
ccctacccga tcgccgagca cctcaccgcc gagatctttg gtctggtgcc tagcctgtgg    1200
tttatcaagc aagccttcga cggcaccacg cccaaggtga tctgcggcac tcccatccct    1260
gctatcgctg gcatcaccac gccctcggcg gaccaggtgc tgggttcgga cctggccgac    1320
cagctgcgca gcctcaacgg caagcagagt gcgttcggca agcccttggg ccccatcaca    1380
ccgccttag                                                            1389
```

<210> SEQ ID NO 15
<211> LENGTH: 1587
<212> TYPE: DNA
<213> ORGANISM: Pseudozyma aphidis

<400> SEQUENCE: 15

```
atgagacatc gtctcgatgg atcgatcgtt ggatcgattg gggcagccat cgcctataaa     60
ggccagccat ccagcccgca agagtatgct agaagcctca agcgacttca ctccctctct    120 tcccacccctt cctcctcatc ccctcgaccc gagccctacc ctctcgctcc cttgcgtctc    180
cctcccacct ttcgaacgat gcgagtgtcc ttgcgctcca ttacctcgct gctggcggcg    240
gcaacggcgg ctgtgctcgc ggctccggca accgagacgc tggaccgacg gcggcgctg    300 cccaacccct acgacgatcc cttctacacg acgccatcca acatcggcac gtttgccaag    360
ggccaggtga tccaatctcg caaggtgccc acggacatcg gcaacgccaa caacgctgcg    420
tcgttccagc tgcagtaccg caccaccaat acgcagaacg aggcggtggc cgacgtggcc    480
accgtgtgga tcccggccaa gcccgcttcg ccgcccaaga tcttttcgta ccaggtctac    540
gaggatgcca cggcgctcga ctgtgctccg agctacagct acctcactgg attggaccag    600
ccgaacaagg tgacggcggt gctcgacacg cccatcatca tcggctgggc gctgcagcag    660
ggctactacg tcgtctcgtc cgaccacgaa ggcttcaaag ccgccttcat cgctggctac    720
gaagagggca tggctatcct cgacggcatc cgcgcgctca gaactacca gaacctgcca    780 tccgacagca aggtcgctct tgagggctac agtggcggag ctcacgccac cgtgtgggcg    840
acttcgcttg ctgactcgta cgcgcccgag ctcaacattg tcggtgcttc gcacggcggc    900
acgcccgtga gcgccaagga caccttaca ttcctcaacg gcggaccctt cgccggcttt    960
gccctggcgg gtgtttcggg tctctcgctc gctcatcctg atatggagag cttcattgag    1020
gcccgattga acgccaaggg tcagcagacg ctcaagcaga tccgcggccg tggcttctgc    1080
ctgccgcagg tggtgttgac ctaccccttc ctcaacgtct tctcgctggt caacgacacg    1140
aacctgctca acgaggcgcc gatcgctggc atcctcaagc aggagacggt ggtccaggcc    1200
gaagcgagct acacggtatc ggtgcccaag ttcccgcgct tcatctggca tgcgatcccc    1260
gacgagatcg tgccgtacca gcctgccgct acctacgtca aggagcaatg tgccaagggc    1320
gccaacatca atttttcgcc ctacccgatc gccgagcacc tcaccgccga gatctttggt    1380
ctggtgccta gcctgtggtt tatcaagcaa gccttcgacg gcaccacacc caaggtgatc    1440
tgcggcactc ccatccctgc tatcgctggc atcaccacgc cctcggcgga ccaggtgctg    1500
ggttcggacc tggccaacca gctgcgcagc ctcaacggca agcagagtgc gttcggcaag    1560
ccctttggcc ccatcacacc accttag                                        1587
```

<210> SEQ ID NO 16

```
<211> LENGTH: 1293
<212> TYPE: DNA
<213> ORGANISM: Pseudozyma hubeiensis

<400> SEQUENCE: 16
atgcatacca gggagacgtt gccggatcca aacgatgatc cttttttacgc ccagccgtcc    60 aacatcgcct cgtacgccaa tggccaagtc attcagtctc gaaaggtaga caccgagatt   120
ggctctatca caacgtgaa caccttccag gtcaagtacc gtaccacaaa cacgcaaaac    180
caggcgcagt ccaacctcgc gactgtctgg atcccctcca agcctgcatc gccgcccaag   240
atcttcagct accaagtcta catggatgcc acccagatcg actgcgctcc gagctacagc   300
tatgtcaccg gcttggacaa gccaggcaag ggcaccgtca tcttggacac acccatcgtc   360
atcagctggg cgctccagca gggctactac gtcgtttcgt ccgacgatga aggtcccaga   420
gctgccttca tcgccgggta cgaggaaggt aaggccgtcc tcgacggcat tcgcgcgctc   480
cagaactacg ccaacttgcc caaggacagc cccatcggaa tgtatggata cagcggaggt   540
gcccatacca ccggatgggc cgttaacctg gctggctcgt acgcttccga gctcaacatc   600
atcggcgctg cctacggagg acttcctgca agcgccaagg acaccttcac cttcctcaac   660
ggcaagagca tcttctccgg ctttgccctt gcgggcgtct cgggccttgc cctcggtcat   720
ccggacatgg aggctttcat caagccgcgc ctcaatgcca agggcaacca aaccttggcc   780
cagatccgaa gccgtggtga atgtatccgg caagttgctc tgggttatcc tttccttgac   840
gtcttctcgc tcgtcaacga caccaacctg ctcaatgaag agcccattgt cagcatcctc   900
aagaccgaaa cgctggtgca agccgaagcg agctacacag ttcccgtccc caaattcccg   960
cgattcatgt ggcacgcgct accagacgag attgttcctt ccaaccggc acaagattat   1020 gtcactgaac agtgtgccaa gggcgccgac attaactgga acgtctaccc aattgccgag  1080
cacatttctg ccgagctctt ggggttgttg cctggtatcg actggttgag caaggcctat  1140
aagggtcaag caccgaaagt tgcatgcggc ggtggtgtac ctgcaacacc tccgcctgcg  1200
gaagacgtgc tcggaggcga cctggcgagc cagttccgct ccctgaacgg caagcagtct  1260
gcttacggca agccttttcaa cgccggattc tga                              1293

<210> SEQ ID NO 17
<211> LENGTH: 1377
<212> TYPE: DNA
<213> ORGANISM: Ustilago hordei

<400> SEQUENCE: 17
atgaggttct tccttggagc tgtgctcgcc ctggccgcag cagccatcgc tgcgctcgct    60
gtacccatgg agaggcgagc tcagttcccg gatcccaacg aggacccctt ctaccagcaa   120
ccgtcgaacg tggccaccta cgccaacggt cagatcatcc gatcacgcaa agctgacacc   180
gacatcggca actcgaacaa ggcccaagcc tttcagctta gctaccgcac caccaacacg   240
cagcagcaag ctcaagccaa cgtcgctacc gtttggatcc ctgctaagcc tgcctctccg   300
cccaagatct tctcctacca ggtctacgag gactcgacgc agctcgactg tgctccaagc   360
tacagctacc tggccggttt tgatcctccc aataaggcta ctaccatcct tgatacttcg   420
ctcatcatcg gctgggcgct tcagcagggt tactacgtcc tctcctccga tcatgagggc   480
cctcgagctg cctttattgc tggttacgaa gagggtatgg ctatccttga cgctattcgt   540
gctttgcaga acttcaggca tctgccaaag gacagcccg ttggcatgta tggttattcg    600
ggaggcgccc atgctactgt ttgggcagag tcgcttgctg gatcctatgc acctgagatc   660
```

```
aacatcatcg ctactgccca cggtggcacc cccttcagta caaaggacac tttcaccttt    720
atcaacggcg gtgtctttgc tggtttcgct attgctggtg tctccggttt ggcccttgtt    780
catcctgcta tgcaagctta catcaagcct cggttgaatg ctcaaggcgt caaggtgttt    840
caacagattc gaagtcgtgc attctgcatc gctcaagtcg ttttcaccta ccctttcacc    900
aacgttttca acctggtcaa cggcaccgac ttgctcaatc aagaaccgat ccgttccatc    960
ctcaaacgag agactcttgt tcaatccgaa gcctcttgcg atgttcctgt tgtccgtgca   1020
cctcgtttca tttggcacgc cgcgctcgat gagatcgttc cgtatgcacc tgccgctcag   1080
tatgttaaag agcaatgcga caagggtgca caaatccatt tcgagacata tcctatcgcc   1140
gaacacttca gcgcagagtt ctttggcctt gttcctgctc tctggttcct tagccaagcc   1200
tacgctggga aagctgccaa gacgtctgc ggaactagca ttcctgccat tcctggcttt   1260
accgttccct ctgcagagga ggtcttgggt gccgaccttg ctaagcagct taagggcttg   1320
agcgccaagg atttgagcgc caaggatttg agcggcaagc acttgccggc tttgtga      1377
```

<210> SEQ ID NO 18
<211> LENGTH: 1377
<212> TYPE: DNA
<213> ORGANISM: Ustilago maydis

<400> SEQUENCE: 18

```
atgaggttca ttgctgttcg ggctatcgtg acgctagcgg ctgcagccgc cgtgtcgctt     60
gcagtgccca cagagcgaag ggcagcgttc gccgatccaa cgacgatct cttctacacc    120 acgccggaca acatcaacac atatgccaat ggtcaggtca tccagtcacg caaggctgat    180
accgatattg ggaacagcaa caaggttgaa gctttccagc ttcaatatcg cactaccaat    240
acgcaaaagg aggcgcaggc caacgttgct accgtatgga tccccaacaa gcccgcttca    300
cctcccaaga tcttctctta tcaggtctat caggactcga cacagctcaa ctgtgctccg    360
agctatagct ttttgaaggg ccttgacaag cctaacaaag ctaccacgat cctcgaagca    420
cccatcatca tcggctgggc gctccaacaa ggtttctacg tcgtctcgtc tgatcacgaa    480
ggcccgcgct catcgttcat tgcgggctac gaggaaggta tggctattct cgacggcata    540
cgtgcgctca gaactacgc caaactgccc acggacagcg cgatcggctt ttacggatac    600
agcggcggtg cccatgcaac cggctgggca gctaatctgg cagggagcta cgctcctgag    660
cacaacatca tcggtgctgc ctacggagga ctgcctgcta gcgccagaga cacattcaac    720
ttcctcaaca aggcgcgtt tgccggcttc gccattgcgg gtgtctcggg tcttgcgctg    780
gcctacccgg acgtggagac ctacatccag tcgcgcctca acgccaaggg agaaaaggtg    840
tttaaacagg tccgaagtcg cggcttctgc attggccaag tggtcctaac ctacccattc    900
gtcgacgcct attcactcat caacgacaca aaccttctca cgaggaacc ggtcgccagc    960 acgttgaaat ccgagacgtt ggttcaggcc gaggctagct acacggttcc tgttcccaaa   1020
ttcccgcgtt tcatctggca tgcgctcttg gacgagattg ttcccttcca ctcggctgcg   1080
acctatgtca aggagcagtg ttcaaagggc gccgacatca actggaatgt ctactcattt   1140
gccgagcaca tctctgccga gcttttcggc ttgctgcctg gtctcgactg gttaaacaag   1200
gcttacaagg gtcaagcacc caaagtgcct tgtggcggag gggctcaaag cgtgatgggt   1260
gcctcaggcc cgcctgcgca ggacgttctg ggagctgacc tggcaagcca actccgatct   1320
ctccagggta agccttctgc gtttggcaac aaacctttgt gctccatctc cccctga      1377
```

<210> SEQ ID NO 19
<211> LENGTH: 1380
<212> TYPE: DNA
<213> ORGANISM: Sporisorium reilianum

<400> SEQUENCE: 19

```
atgagattct tgcgcagac cctagtcgcg ctggcagccg ccgccacggt ttcgctcgct    60
gcgcccttgg agcgaagggc gcagttccct gaccccaacg acgacccgtt ctactcggcg   120
ccggccaaca tcggctcgta cgtcaacggc caggtgatcc agtcgcgctc ggcgaccacg   180
gacatcggca cgtcgaacaa tgcggcgtcg ttccaactgc tgtaccgaac caccaacacg   240
tcgaacctgc ccgaggcgac ggtggcgacc gtgtggatac ctgccaagcc ggcgtcgccg   300
cccaagatct tctcgtacca ggtgtacgag gatgctacgc agctcaactg cgctccgtcg   360
tacagctatc tctcgggctt ggacgagcct ggcaagggca ccgtgatcct ggacacgccc   420
atcgtcatca gctgggcgct gcagcagggc tactacgtcg tgtcggccga ccacgagggg   480
cccaaggcgg cgttcatcgc tggatgccag gagggtcgcg ccatcctcga cggcgtgcgc   540
gcgctgagga acttccagaa cctggcttcg aacagcgcgg tcggattcta cggctacagc   600
ggcggtggac acgcgacggg ctgggcggtg agcctggctg gctcgtatgc tccggacgtc   660
aacatcatcg tgctgcgta cggtggagtg ccgacgagca cgagggacat cttcaacttc   720
ctcaacggcg tgcctttgc tggattcgcc gtggcgggtg tctctggcct cggactggcg   780
tatcccgagc tggaggcgta cattgaacct cgactgaacg ccaaggggca ggacgcgctc   840
aagcgcttcc gcagccgcgg atactgtatc ggccaagtgg tgacgagcga aaactttgtc   900
gacatctaca cgctggtcaa cgacagcaac atcctcaacg agcccatccc ttcgcaggtg   960
ctggccaagg agacgctgct gcagacgcag gcgagctaca cggtgcccgt gcccaagtcc  1020
ccgcgattca tctggcatgc gctcgaggac gagattgtgc cgttcaagcc ggcgcagcag  1080
tatgtgacgg agcagtgtgc caaaggcgcc aacatcaact ggaacgtgtt cccgatcgct  1140
gagcacatca gtgctgagct cttcggcttg gtgcccggtc tcgactggct gagcaaggcc  1200
tacaggggac aggcgcccaa ggtgatctgc ggttcgagca ttcccgccat cacaggagtc  1260
aattcgccgt cggcacagca agtgcttgga gctgatctgg cacagcagct gagcaacctc  1320
aacggcaagc agtcggcgtt tggcaagcct tacgggccca tcacacctcc cacggcctga  1380
```

<210> SEQ ID NO 20
<211> LENGTH: 1380
<212> TYPE: DNA
<213> ORGANISM: Sporisorium scitamineum

<400> SEQUENCE: 20

```
atgaagttct ttccgcaagc cgtcgtcgcg ctagcagccg cagccacggc agcactggct    60
gtgcccatgc agaagagggc gcaatacccca gaccccgaacg acgatccttt ctactcggtg  120
ccagccaaca ttggctcgta ctccaacggt caggtgatcc agtcgcgttc ggccaccacc   180
gatatcggta acgctaacaa tgcgctctcg tttcagttgc tctaccgaac caccaacacc   240
tcgaaccaag ccgacgcgac tgtagccacc gtgtggatcc ccgccaagcc agcgtcaccg   300
cccaagatct tctcgtacca ggtgtatgaa gacgcaacgc agctcgactg tgctccatcg   360
tacaactacc tgtctggact cgaacagccc ggcaaggcca ccgtcatcct cgatacgccc   420
attatcatcg gctgggcgct gcagcagggc tactacgttg tctcggccga ccacgagggt   480
cccaaggcgg cgttcatcgc tggataccaa gagggtaggg ccatcctgga cggtattcgt   540
```

```
gctctgagga actttaagga cctgccttcg agcagcgccg tcggatttta cggctacagc    600
ggtggtggac acgctactgg ctgggcggtc aacctggccg actcgtacgc tccgacgtc    660 aacattatcg gtgctgccta cggcggattg cctgccagca cgagggacat tttcaacttc    720
ctcaacggag gtgtctttgc tggtttcgcg gtcgctggtg tctctggcct cggacaggcg    780
taccctgagc tggaggcttt tgtcgagcct cgactcaacg ccaagggtca ggaggcgctc    840
aagaagttcc gtagccgtgg cttctgcatt ggacaagtgg tgaccaacga aactttgtc    900 gacatctaca cgctcgtcaa cgacagcaac atcctcaacc agccgattcc gtctgaggtc    960
ttggcgaaag aaacgctgct ccagtcgcag gcgagctaca cggttccggt tcccaagttc   1020
ccacgattca tctggcatgc gctcgaggac gagatcgttc ccttcattcc tgcgcagaag   1080
tacgtgcagg agcagtgtgc caagggtgcc aacatcaatt ggaacgtctt ccccatcgct   1140
gagcacctta ctgctgaaat ctttggcttg gtgcccggtc tctactggct tagccaagcg   1200
tacgctggta aagcacccaa ggtgacgtgc ggtggtggta ctcctgccat cacgggtgtc   1260
acgtcgccgt cggcacagca agtgttggga gccgatctgg cgaagcagct gagcagtctc   1320
aacggcaagc agtccgcttt cggcaagcca tttggttcca tcacgcctcc gacatcgtaa   1380
```

<210> SEQ ID NO 21
<211> LENGTH: 1374
<212> TYPE: DNA
<213> ORGANISM: Melanopsichium pennsylvanicum

<400> SEQUENCE: 21

```
atgaggttct tctctcgagc agtcattgga ctggctgcag tagccactgc tgcaatcgcc     60
atgcccacgc acaagcgtgc tgctttccct gatcccaatg acgattcctt ctaccagaat    120
cccgccaaca tcgccactta cgcaaacggt caaatcatcc agtcgcgcaa cgtcgttacc    180
gacattggca acaacaataa ggccgactcg ttccaacttt cctaccgcac caccaacacc    240
caaaaagacg ccgttgctaa cgtagccacc attttcatcc ccagcaagcc cgcctctcct    300
cccaagatct tctcgtacca ggtgtacgaa gactcgactc agctgaattg tgcacccagc    360
tacaattacc tcactggctt cgatgagccc aacaaggtta ccacgtctct agacacaccc    420
atcatcatca gttgggccct caatcaaggc tactacgtcg tctcctctga tgccgaggga    480
caacgctccg ctttcattgc tggttacgaa gagggtatgg ccatccttga cgcaattcgt    540
gcacttaaga attacaagtc tttgcccaaa gacaccgaga ccgccttata tggctatagt    600
ggtggagccc acgcaaccgc ctgggctgtt agcctttccg catcgtacgc tcctgacatc    660
aacatcatcg gtgctgccta tggaggtaca cccaccagcg ccaaggacac tttcaattac    720
ctcaacaagg gcctcttgc tggcttcgct gtttctggtg tctcaggtct cgcccttgct    780 caccccggata tggagagttt tatcgagcct cgcctcaatg ccgtgggtca gcaggtcttc    840
cagaaggtcc gaagccgcgg ttactgtatc gttcaggttt cgaccaacaa caatttacgc    900
gacgtctaca cgcttgtcaa cgacaccaat ttgctcaacg aggaacccat caagagcatt    960
cttgcgctcg agacgctggt tcaggctgag gctagctaca cagtgccagt cccaaagttc   1020
ccgaggttca tgtggcacgc tttgcctgac gaaattgtgc cattccagcc tgctgctgac   1080
tacgtccagg aacagtgctc gaaaggagcc aacatcaatt ggaatgtgta tcctattgct   1140
gagcacgtca cagctgagat cttcggtatc atccccgccc tcgactggct cggcaaggtc   1200
tacagcggta atgcgccaaa ggtggcctgc ggggggcggtg ttccaggtat tgctggtgtt   1260
```

| | |
|---|---|
| acaactcccc ctgccaacga cgtgctcggt tctgcgcttg ctcagcagct tggcaacctt | 1320 |
| agcggtaaga cgtcggcatt cgggaagcct ttcggcacca tcacgccttc ttaa | 1374 |

<210> SEQ ID NO 22
<211> LENGTH: 1377
<212> TYPE: DNA
<213> ORGANISM: Kurtzmanomyces

<400> SEQUENCE: 22

| | |
|---|---|
| atgcgcttct tccttcgagc cgtgctcgga ctggcggtca cagcgactgc agcactcgct | 60 |
| gccccctgg agcctagagc cgcactcccg gatccaaatg aagatccgtt ttactcgaca | 120 |
| ccgtccaata tcgagacgtt cgccaacggt caaatcatcc agtcgcgcaa ggttcccacc | 180 |
| gacattggca actcgaacaa tgccgcttcg taccagctgt cgtaccgcac cacaaacaca | 240 |
| caagaggatg ctgttgctaa cgttgctacc atctggatcc cggccaagcc atcgtcaccg | 300 |
| ccacgtatct tcacttatca ggtttacgag gactcgaccc aactcgattg tgcacctagc | 360 |
| tacagctacc ttactggata cgatcagccc aacaaggcaa cggctgttct cgacactccg | 420 |
| atcgtcatca gctgggcctt gcaacagggc tattatgtgg tctctgcaga ccatgaagga | 480 |
| gcccgctctg ccttcatcgc tggctacgaa gaaggcatgg cggcccttga cggtattcgt | 540 |
| gcgctcagaa attacgcaaa actaccacag gacagcgctg tcggagccta cggctattct | 600 |
| ggaggagccc atgctaccgt ttgggcaact tccttggctg ctgcctatgc tcctgagatc | 660 |
| aacttcatcg gtgctgctca tggtggaaca cccgttagcg cgaaggatac cttcactttc | 720 |
| atcaacggcg gtttcttcgc tgggtttgcc attgctggtg tctcaggttt ggccaacgct | 780 |
| caccctgata tggaagcctt catccagccc cgtctgaacg ctgagggtgt caaaacactc | 840 |
| aaacagatcc gaagccgagg cttctgcctt cccgaggtgg tcactactta tcctttcaag | 900 |
| aacgtcttcg ccctggtcaa tgacacgaac ctgctcactg agcagcccat ctccggcatc | 960 |
| ttgcagcaag agacgcttgt tcaatcggag gcgagctacg ctgtacctgt ccctaagttt | 1020 |
| ccccgcttct tgtggcatgc tgctctcgac gagatcgtcc cctacgtacc tgtcaccgag | 1080 |
| tatgtcaaag aacagtgtgc caagggcgcc aacatcaact tcaacaccta cccgatcgcc | 1140 |
| gagcatctca ctgccgaaat cttcggtctc gttccaggtc tttggttctt gagccaggct | 1200 |
| tacgagggca aggcaccggc ggttcagtgc ggaactgcac ttcctgcggc tccttctgct | 1260 |
| caacaggtac ttggaaacga cttggccaac caattgagca gcctcaacgg caagcaatct | 1320 |
| ccgtttggca agccattcgg ccccataagc ccgacttcgc ttgacaagtt gctgtag | 1377 |

<210> SEQ ID NO 23
<211> LENGTH: 33
<212> TYPE: DNA
<213> ORGANISM: Artificial Sequence
<220> FEATURE:
<223> OTHER INFORMATION: primer

<400> SEQUENCE: 23

| | |
|---|---|
| ctctagagga tccccatgcg agtgtccttg cgc | 33 |

<210> SEQ ID NO 24
<211> LENGTH: 33
<212> TYPE: DNA
<213> ORGANISM: Artificial Sequence
<220> FEATURE:
<223> OTHER INFORMATION: primer

<400> SEQUENCE: 24

```
gtagggagcg taccccctaag gcggtgtgat ggg                                    33

<210> SEQ ID NO 25
<211> LENGTH: 26
<212> TYPE: DNA
<213> ORGANISM: Artificial Sequence
<220> FEATURE:
<223> OTHER INFORMATION: primer

<400> SEQUENCE: 25
gtagtcgacg tcgcctcgga aagatc                                             26

<210> SEQ ID NO 26
<211> LENGTH: 24
<212> TYPE: DNA
<213> ORGANISM: Artificial Sequence
<220> FEATURE:
<223> OTHER INFORMATION: primer

<400> SEQUENCE: 26
caggtcgaca tccgctctct cttc                                               24

<210> SEQ ID NO 27
<211> LENGTH: 29
<212> TYPE: DNA
<213> ORGANISM: Artificial Sequence
<220> FEATURE:
<223> OTHER INFORMATION: primer

<400> SEQUENCE: 27
ctgtctagag atgatggatg gggagtgtg                                          29

<210> SEQ ID NO 28
<211> LENGTH: 25
<212> TYPE: DNA
<213> ORGANISM: Artificial Sequence
<220> FEATURE:
<223> OTHER INFORMATION: primer

<400> SEQUENCE: 28
tcctctagat aatttttggg atgag                                              25

<210> SEQ ID NO 29
<211> LENGTH: 41
<212> TYPE: DNA
<213> ORGANISM: Artificial Sequence
<220> FEATURE:
<223> OTHER INFORMATION: primer

<400> SEQUENCE: 29
atgcctgcag gtcgacgaaa taactcagca catcgccctt g                            41

<210> SEQ ID NO 30
<211> LENGTH: 34
<212> TYPE: DNA
<213> ORGANISM: Artificial Sequence
<220> FEATURE:
<223> OTHER INFORMATION: primer

<400> SEQUENCE: 30
atgcctgcag gtcgacttgt tggaagatgg gatg                                    34

<210> SEQ ID NO 31
<211> LENGTH: 39
<212> TYPE: DNA
```

```
<213> ORGANISM: Artificial Sequence
<220> FEATURE:
<223> OTHER INFORMATION: primer

<400> SEQUENCE: 31
atggggatcc tctagatgat gttttttgatg tatgatatg                         39

<210> SEQ ID NO 32
<211> LENGTH: 35
<212> TYPE: DNA
<213> ORGANISM: Artificial Sequence
<220> FEATURE:
<223> OTHER INFORMATION: primer

<400> SEQUENCE: 32
atggggatcc tctagatcac gattttgcta accag                              35
```